US009925118B2

(12) United States Patent
Holtwick et al.

(10) Patent No.: US 9,925,118 B2
(45) Date of Patent: Mar. 27, 2018

(54) Z-SHAPED FLUID CHANNEL ARRANGEMENT

(75) Inventors: Marc Holtwick, Frankfurt am Main (DE); James Alexander Davies, Warwickshire (GB); Simon Lewis Bilton, Warwickshire (GB); David Moore, Leicestershire (GB); Steven Wimpenny, Warwickshire (GB); Christopher Nigel Langley, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 843 days.

(21) Appl. No.: 14/113,760

(22) PCT Filed: Apr. 26, 2012

(86) PCT No.: PCT/EP2012/057703
§ 371 (c)(1),
(2), (4) Date: Oct. 24, 2013

(87) PCT Pub. No.: WO2012/146685
PCT Pub. Date: Nov. 1, 2012

(65) Prior Publication Data
US 2014/0046267 A1 Feb. 13, 2014

Related U.S. Application Data

(60) Provisional application No. 61/480,063, filed on Apr. 28, 2011.

(30) Foreign Application Priority Data

Jul. 8, 2011 (EP) .................................... 11173267

(51) Int. Cl.
A61M 5/00 (2006.01)
A61J 1/14 (2006.01)
(Continued)

(52) U.S. Cl.
CPC .............. *A61J 1/1475* (2013.01); *A61M 5/19* (2013.01); *A61M 5/24* (2013.01); *A61M 5/2448* (2013.01);
(Continued)

(58) Field of Classification Search
CPC A61M 5/24; A61M 5/19; A61M 5/50; A61M 5/2448; A61M 5/345; A61M 5/348;
(Continued)

(56) References Cited

U.S. PATENT DOCUMENTS 533,575 A 2/1895 Wilkens
5,147,323 A 9/1992 Haber et al.
(Continued)

FOREIGN PATENT DOCUMENTS

EP 0937471 A2 8/1999
EP 0937476 A2 8/1999
(Continued)

*Primary Examiner* — Theodore Stigell
(74) *Attorney, Agent, or Firm* — McDonnell Boehnen Hulbert & Berghoff LLP

(57) ABSTRACT

The invention is related to a manifold comprising at least two valve receptacles, further comprising a fluid groove arrangement comprising at least two fluid grooves, wherein a first fluid groove of the at least two fluid grooves has a starting point near a first valve receptacle of the at least two valve receptacles and an end point near a second valve receptacle of the at least two valve receptacles and wherein a second fluid groove of the at least two fluid grooves has a starting point near a second valve receptacle of the at least two valve receptacles. The invention is further related to an apparatus comprising a manifold of the aforementioned kind and further comprising an inner body of a dispense interface.

10 Claims, 19 Drawing Sheets

(51) Int. Cl.
*A61M 5/19* (2006.01)
*A61M 5/24* (2006.01)
*A61M 5/34* (2006.01)
*A61M 5/50* (2006.01)
*A61M 5/31* (2006.01)
*A61M 5/20* (2006.01)
*A61M 5/178* (2006.01)

(52) U.S. Cl.
CPC .......... *A61M 5/345* (2013.01); *A61M 5/2066* (2013.01); *A61M 5/348* (2013.01); *A61M 5/50* (2013.01); *A61M 2005/1787* (2013.01); *A61M 2005/2496* (2013.01); *A61M 2005/3125* (2013.01); *A61M 2005/3128* (2013.01); *A61M 2205/502* (2013.01)

(58) Field of Classification Search
CPC ........ A61M 2005/3128; A61M 5/2066; A61M 2005/1787; A61M 2005/2496; A61M 2005/3125; A61M 2205/502; A61J 1/1475
See application file for complete search history.

(56) References Cited

U.S. PATENT DOCUMENTS

| | | |
|---|---|---|
| 5,199,949 A | 4/1993 | Haber et al. |
| 5,226,895 A | 7/1993 | Harris |
| 5,279,586 A | 1/1994 | Balkwill |
| 5,298,023 A * | 3/1994 | Haber ................. A61M 5/2448 604/191 |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,423,752 A | 6/1995 | Haber et al. |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2009/0275916 A1 | 11/2009 | Harms et al. |

FOREIGN PATENT DOCUMENTS

| | | |
|---|---|---|
| WO | 9403606 A1 | 2/1994 |
| WO | 9406487 A1 | 3/1994 |
| WO | 9614097 A1 | 5/1996 |
| WO | 9938554 A1 | 8/1999 |
| WO | 0110484 A1 | 2/2001 |
| WO | 2011067187 A1 | 6/2011 |

* cited by examiner

US 9,925,118 B2

Z-SHAPED FLUID CHANNEL ARRANGEMENT

CROSS REFERENCE TO RELATED APPLICATIONS

The present application is a U.S. National Phase Application pursuant to 35 U.S.C. § 371 of International Application No. PCT/EP2012/057703 filed Apr. 26, 2012, which claims priority to U.S. Provisional Patent Application No. 61/480,063, filed Apr. 28, 2011 and European Patent Application No. 11173267.3 filed Jul. 8, 2011. The entire disclosure contents of these applications are herewith incorporated by reference into the present application.

FIELD OF INVENTION

The present patent application relates to medical devices for delivering at least two drug agents from separate reservoirs. Such drug agents may comprise a first and a second medicament. The medical device includes a dose setting mechanism for delivering the drug agents automatically or manually by the user. In particular, the present invention relates to a fluid channel arrangement as for example usable in such a medical drug delivery device.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

With the drug delivery device for the sequential injection of multiple medicaments generally having a separate reservoir for each medicament, but only a single injection needle, each medicament is held back in its reservoir by a separate valve. This respective valve is arranged in the dispense interface of the drug delivery device, with each medicament entering a common conduit leading to the needle after having passed its respective valve and the post-valve section of its dedicated conduit. The volume of this common conduit is part of the ullage, i.e. of the volume downstream from a respective valve. In the case of a dispense interface for delivering two different drugs, the conduit arrangement after the respective valves may be represented by a Y-arrangement, with each valve at the end of a lateral arm of the Y-arrangement and the needle positioned at the base of the Y-arrangement.

In such an arrangement the lateral arms represent a respective dedicated conduit for the medicament from the associated reservoir, whereas both medicaments have to sequentially pass the base of the Y-arrangement, i.e. the common conduit. When two drugs are to be sequentially administered, the first medicament passes its dedicated conduit and then passes the common conduit. Afterwards, the second medicament passes its respective dedicated conduit and then the common conduit. In order to pass the common conduit, the second medicament will push along or absorb any of the first medicament that may remain in the common conduit, thereby also causing injection of this remainder of the first medicament. The second medicament will not, however, similarly activate the portion of the first medicament remaining in the dedicated conduit of the first medicament, because the second medicament does not pass this conduit. Because the particular distribution of the first medicament between the first medicament's dedicated conduit and the common conduit may be variable, for example due to production tolerances, uncertainty remains about the applied volume of the first medicament. This makes an exact dosage of the first medicament hard.

Thus it is an object of the invention to provide a dispense interface for a drug delivery device or a component thereof with which the dosage accuracy of a drug delivery device for sequentially delivering multiple medicaments can be improved. It is a further object of the invention to provide a dispense interface for a drug delivery device or a component thereof that may provide a higher dosing accuracy of a first medicament compared to the dosing accuracy of a second medicament.

This problem of the invention is solved by a manifold comprising at least two valve receptacles and a fluid groove arrangement comprising at least two fluid grooves, wherein a first fluid groove of the at least two fluid grooves has a starting point near or at a first valve receptacles of the at least two valve receptacles and an end point near or at a second valve receptacle of the at least two valve receptacles, wherein a second fluid groove of the at least two fluid grooves has a starting point near or at a second valve receptacle of the at least two valve receptacles.

By means of this arrangement, the fluid path of the first medicament is arranged downstream of the fluid path of the second medicament to the full extent, thereby allowing the second medicament to scoop up all remainders of the first medicament in its fluid path. The principle of operation is exemplarily described thus: The valve receptacles are configured to receive the respective valve for the first and second (and potentially further) medicament, with the fluid grooves providing paths for the fluid flow from the valves to the needle. In the case of two medicaments, the valve of the medicament to be injected first, i.e. the first medicament, is received in the second valve receptacle, for example a simple cavity, whereas the valve of the medicament to be injected second, i.e. the second medicament, is received in the first valve receptacle. The valve receptacles only serve for positioning and fixing the valves and not for the flow of liquid in or through the valve receptacles.

Opening the valve of the first medicament allows the first medicament to flow from the valve to the second fluid groove and from there to the needle. After injection of the first medicament, some substance of the first medicament remains in the second fluid groove. Subsequently, the valve of the second medicament is opened, thereby allowing the second medicament to flow from the valve to the first fluid groove. From there, the second medicament continues to flow to the second fluid groove and from there to the needle. Consequently, any portion of the first medicament remaining in the second fluid groove is pushed along by the second medicament or absorbed with little or no of the first medicament remaining in the second fluid groove. Therefore the first medicament is injected in full and an exact dosage becomes possible.

This effect is also realized in full in the case that at least some of the first medicament enters the first fluid groove in the upstream direction instead of the second fluid groove. Even in this situation, the second medicament flowing in the downstream direction in the first fluid groove will push along or absorb any remains of the first medicament in the first fluid groove.

The manifold may be a component to guide fluid flow in the dispense interface of a drug delivery device. The manifold may be any three-dimensional structure. It may in particular be a flat, plate-like structure of arbitrary shape with any indentations, projections or more complicated arrangements on its surface. The manifold may be of any material, in particular a synthetic material.

The fluid groove arrangement may comprise any number of fluid grooves, which may be any indentations on the surface of the manifold which permit the passing of fluid along the surface of the manifold. The fluid grooves of the fluid groove arrangement are arranged such that there are only two directions for any fluid in the fluid groove arrangement to flow, namely either in the upward or in the downward direction. In other words, the fluid groove arrangement does not comprise a T-junction, i.e. a three-way junction. In yet other words, the fluid groove arrangement in its entirety may comprise a single starting point, i.e. the point of inflow furthest in the upstream direction, and a single end point, i.e. the point of outflow furthest in the downstream direction.

The fluid grooves may be arranged in any linear or curved way on the manifold. The end point of the first fluid groove near the second valve receptacle may or may not coincide with the starting point of the second fluid groove near the second valve receptacle. Either way, fluid flow from the first fluid groove to the second fluid groove is possible when the manifold is arranged in the dispense interface of the drug delivery device. The valve receptacles may be valve receiving means.

In a preferred embodiment of the invention, the manifold comprises at least one filling block, wherein there is an at least indirect fluid connection between the second fluid groove and the at least one filling block. The filling block may be any structure on the surface of the manifold which enables fluid flow out of the filling block. The filling block does not have to be a closed structure but may be a structure that becomes closed in combination with a corresponding counterpart of a dispense interface. The filling block may be the fluid flow interface from the manifold through the dispense interface of which the manifold is a component and yet further through the needle of the drug delivery device comprising the dispense interface. The second fluid groove may be in direct fluid connection with one or more filling blocks. It may also be that the second fluid groove is in fluid connection with one or more further fluid grooves, which in turn are connected with the one or more filling blocks, whereby the second fluid groove may be in indirect connection with the one or more filling blocks.

In a further preferred embodiment of the invention, the at least two valve receptacles are valve cavities. The valve cavities may be any indentations or other structural features which may be used for providing at least part of a cavity for a valve which may be arranged in combination with the manifold. This has the advantage of providing a simple but effective valve receptacle.

In a further preferred embodiment of the invention, the at least one filling block is a rectangular protrusion.

In a preferred embodiment of the invention, the at least one filling block and the fluid groove arrangement are arranged on a top surface of the manifold.

In a further preferred embodiment of the invention, each of the at least two valve receptacles is positioned in a respective convex protrusion on a surface of the manifold. In this embodiment, the starting and end point of the first fluid groove being near the first valve receptacle and the second valve receptacle, respectively, preferably means that the fluid groove cuts into the convex protrusion around the respective valve receptacle, without actually reaching all the way to the valve receptacle. The same preferably applies, mutatis mutandis, to the starting point of the second fluid groove with respect to the second valve receptacle. Positioning each of the at least two valve receptacles in a respective convex protrusion enables a simple construction of a diaphragm valve using the manifold and a suitable counterpart of the dispense interface.

In yet a further preferred embodiment of the invention, each of the at least two valve receptacles is positioned in the centre of the respective convex protrusion.

In a still further preferred embodiment of the invention, the manifold comprises two valve receptacles.

In a further preferred embodiment, the outward appearance of the manifold is Y-shaped. A Y-shape is basically a star shape with three branches that connect in a central point. Thus, a manifold may be Y-shaped by having three flat branches joined at the middle. Two branches of the Y-shape in the direction of the reservoirs may be designated as arm branches whereas the third branch in the direction of the needle may be designated as base branch. Each branch may have a different length. Each valve receptacle and the filling block may be arranged on a different respective branch.

In yet a further preferred embodiment, the filling block is provided near the base of the manifold, the base being a distal end of the manifold. The distal end of the manifold is the end towards which the medicaments are injected by the drug delivery device flow.

The problem of the invention is further solved by an apparatus comprising a manifold according to the invention and further comprising an inner body of a dispense interface, at least two valve structures, each at least partially received by one of the at least two valve receptacles, further comprising at least two reservoirs defined by the inner body, wherein each valve structure is configured to provide a fluid seal between a respective reservoir of at least two reservoirs and the fluid groove arrangement in a first state, and wherein each valve structure is further configured to enable fluid flow from a respective reservoir of the at least two reservoirs to the fluid groove arrangement in a second state.

The inner body of the dispense interface may be a structure of the dispense interface configured to receive the manifold. In particular, the inner body defines a respective reservoir for each medicament to be delivered by the drug delivery device. The at least two valve structures provide the respective points of inflow of each medicament to be injected by the drug delivery device to the manifold. The at least two valve structures may be valve means. Each valve structure can change between at least two states. In the first state, which may be designated the closed state, the valve structure blocks fluid flow from the reservoir of the respective medicament to the fluid groove arrangement. In the second state, which may be designated the open state, the valve structure enables fluid flow from the reservoir of the respective medicament to the fluid groove arrangement.

In a preferred embodiment of the invention, the inner body comprises a holding chamber configured for housing the at least one filling block and further configured for fluid outflow from the inner body. The holding chamber may form a closed cavity by interlocking with the filling block. The holding chamber may be connected with the filling block, for example by welding or gluing, when the dispense interface is assembled. The holding chamber is the fluid outflow in the direction of the needle of the dispense interface.

In a further preferred embodiment, the inner body is arranged with the manifold such that any fluid flowing from the at least two reservoirs via at least one of the at least two valve structures to the holding chamber flows at least through the second fluid groove of the at least two fluid grooves. This means that independent of the valve through which any given fluid enters the fluid groove arrangement, it will pass the second fluid groove. Since the second fluid groove provides the fluid connection for the first medicament to be dispensed via the holding chamber, any subsequent fluid will scoop up any remaining portions of the first medicament in its path in their entirety. Therefore no parts of the first medicament will remain left in the fluid groove arrangement.

In yet a further preferred embodiment of the invention, the at least two valve structures comprise a first valve at least partially received by the first valve receptacle, which first valve is configured to block fluid flow from a first reservoir to the starting point of the first fluid groove in a first state and to enable fluid flow from the first reservoir to the starting point of the first fluid groove in a second state.

In a further preferred embodiment of the invention, the at least two valve structures comprise a second valve at least partially received by the second valve receptacle, which second valve is configured to block fluid flow from a second reservoir of the at least two reservoirs to the starting point of the second fluid groove in a first state and to enable fluid flow from the second reservoir to the starting point of the second fluid groove in a second state.

In a yet further preferred embodiment of the invention, the at least two valve structures comprise at least one diaphragm valve, each diaphragm valve comprising a circular protrusion configured to be seated in a respective valve receptacle, wherein each diaphragm valve is substantially cup-shaped, and wherein in its respective first state each diaphragm valve is facing the respective valve receptacle with the diaphragm valve's convex side and is un-stressed. Each diaphragm valve comprises a cup-shaped, for example a semispherical membrane with a circular protrusion at its apex. In the un-stressed, closed state this membrane may be placed opposite a convex protrusion with the circular protrusion received by the valve receptacle, for example a valve cavity, the membrane and the convex protrusion thereby forming an hourglass-shape. The medicament enters the valve in the forward direction from the concave side of the membrane and is contained by this concave side of the membrane. In the un-stressed state, there is no or no significant fluid pressure acting on this membrane in the forward direction, i.e. from the concave side of the membrane.

In yet another preferred embodiment of the invention, each diaphragm valve is configured to invert its cup-shape under fluidic pressure and the cup-shape of each diaphragm valve is inverted in its respective second state. When sufficient fluid pressure is applied to the membrane of the diaphragm valve in the forward direction, i.e. from the concave side of the diaphragm valve, corresponding to the side of the respective reservoir defined by the inner body of the dispense interface, the membrane of the diaphragm valve inverts, thereby now projecting a convex side in the direction in which in the first state the concave side was facing and vice versa. Therefore in the inverted state, with the circular protrusion still remaining in the valve receptacle, the diaphragm valve and a preferably present convex protrusion do not, together, form an hourglass shape but rather a shape of two stacked cups, i.e. with the convex protrusion and the membrane of the diaphragm valve both having their convex side in the same direction. With the membrane inverted, the diaphragm valve does no longer restrain fluid flow in the forward direction. Therefore fluid, in particular a medicament, can flow out from the sides of the diaphragm valve and enter, for example, a fluid groove which has a starting point or end point in the preferably present convex protrusion associated with the diaphragm valve.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
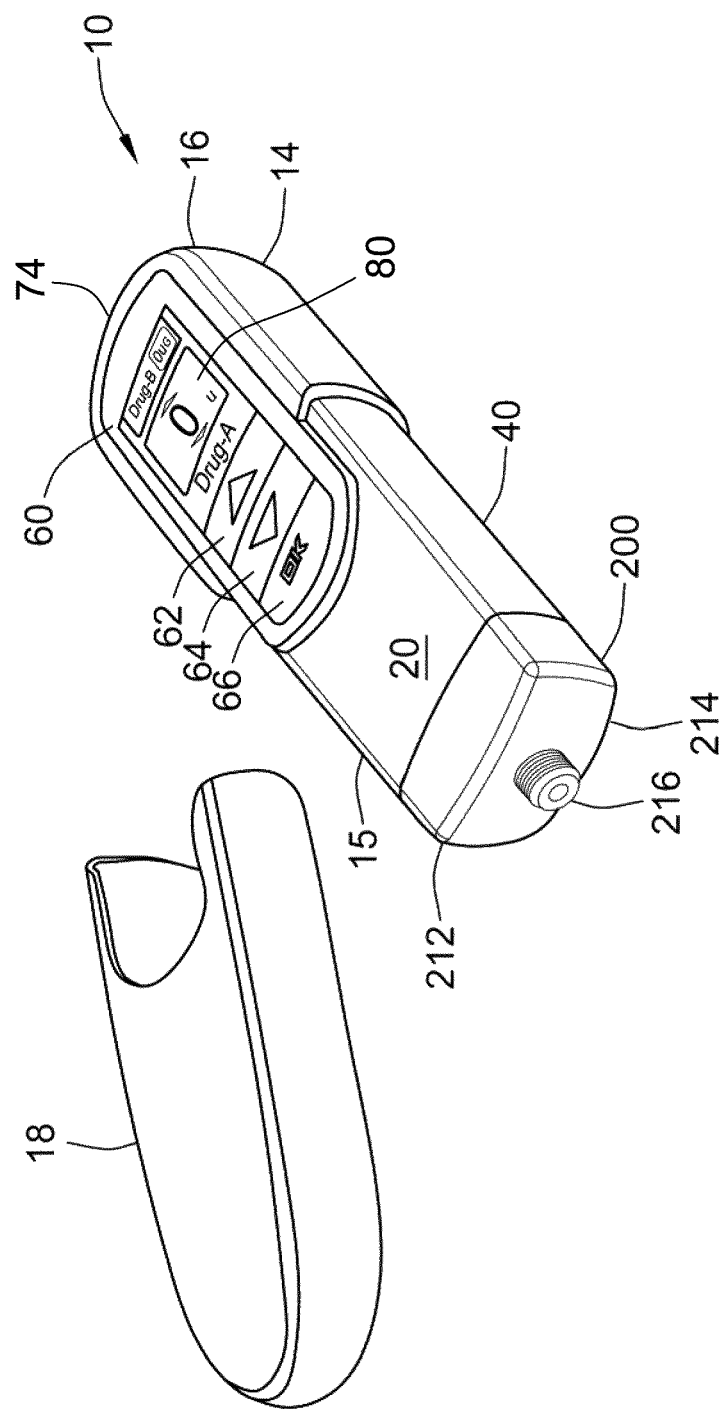
FIG. 1 illustrates a perspective view of a delivery device with an end cap of the device removed.
Figure 2:
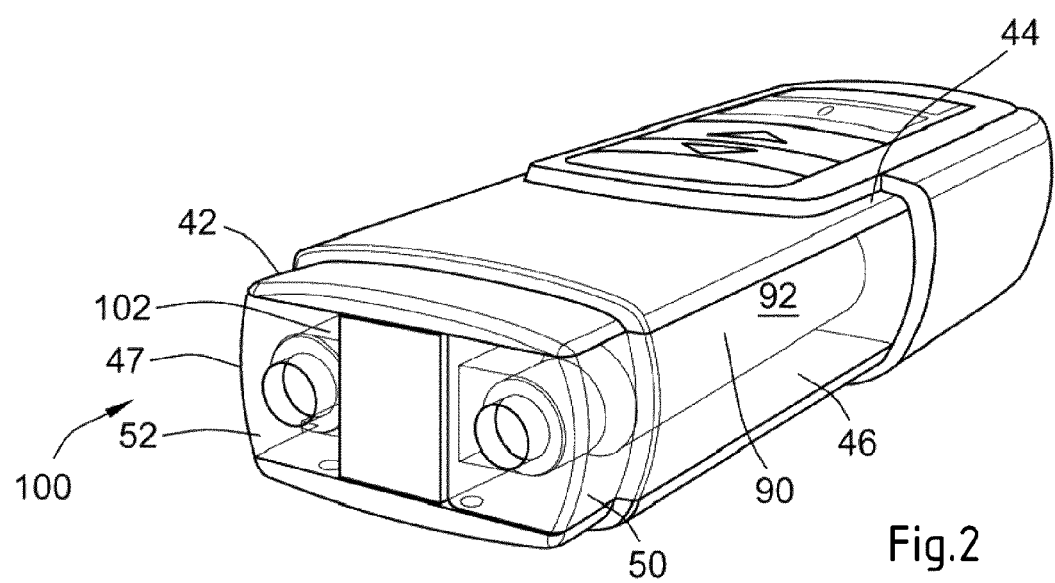
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
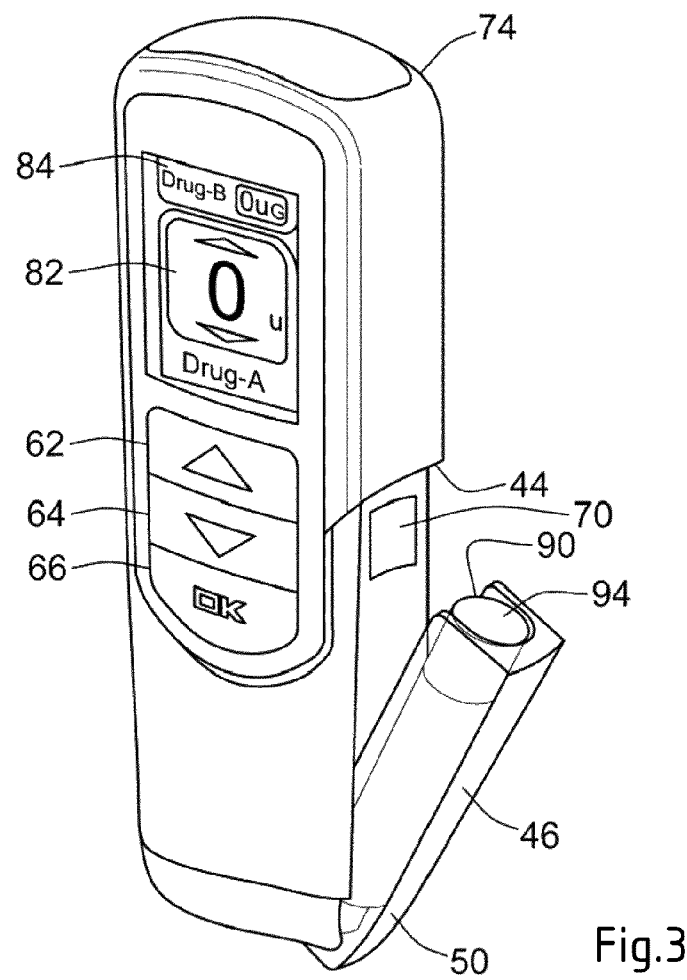
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
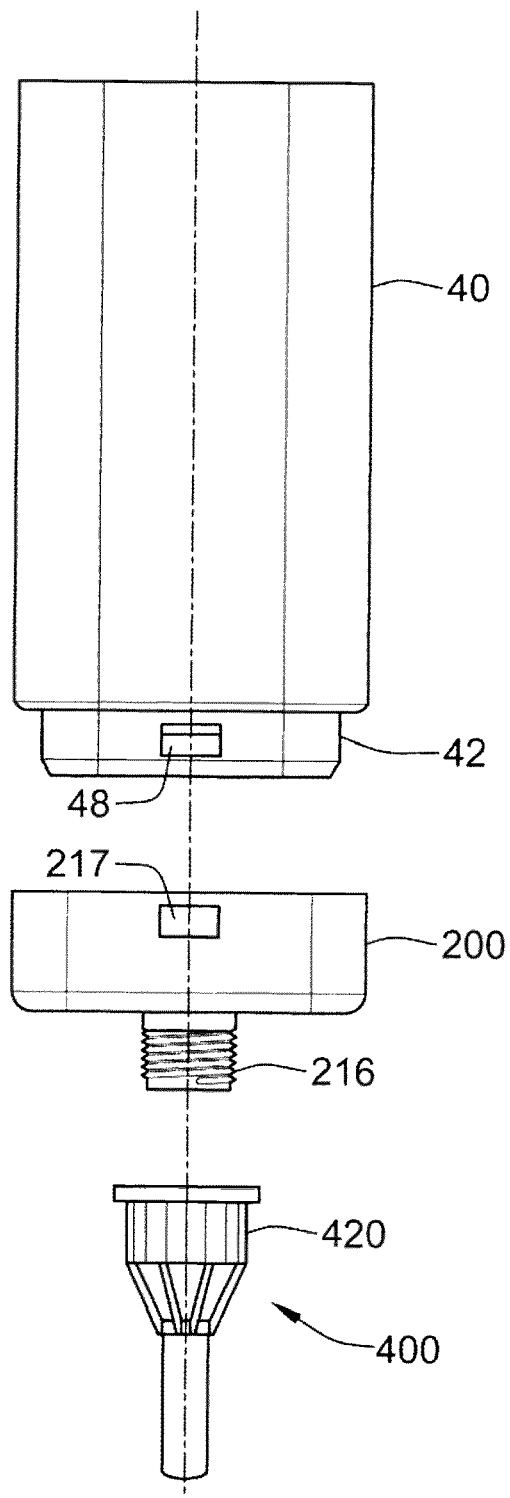
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
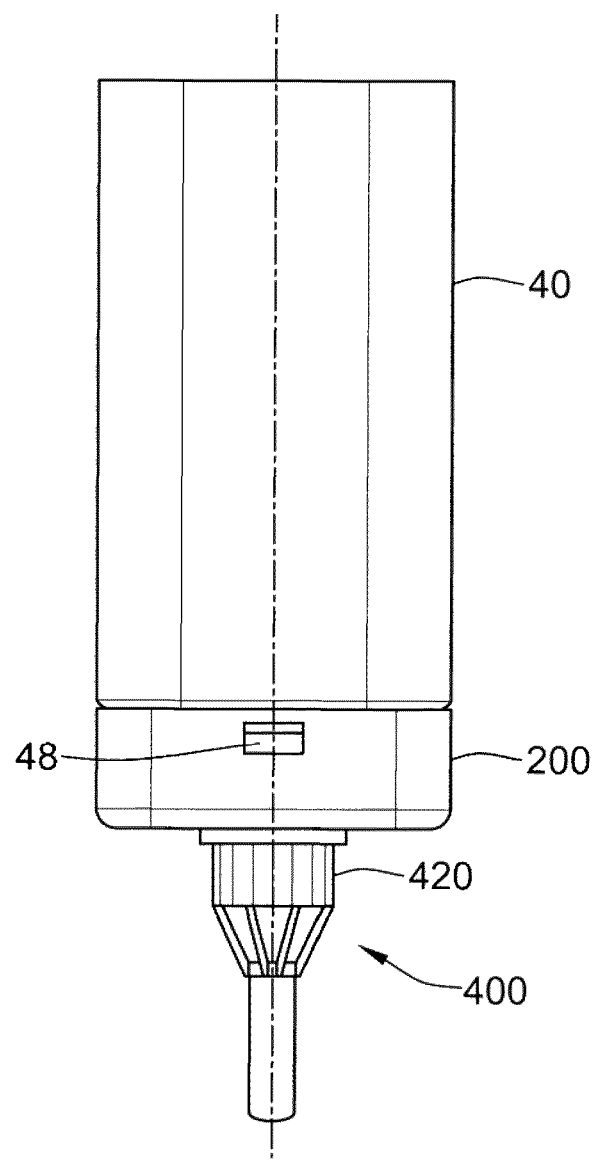
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
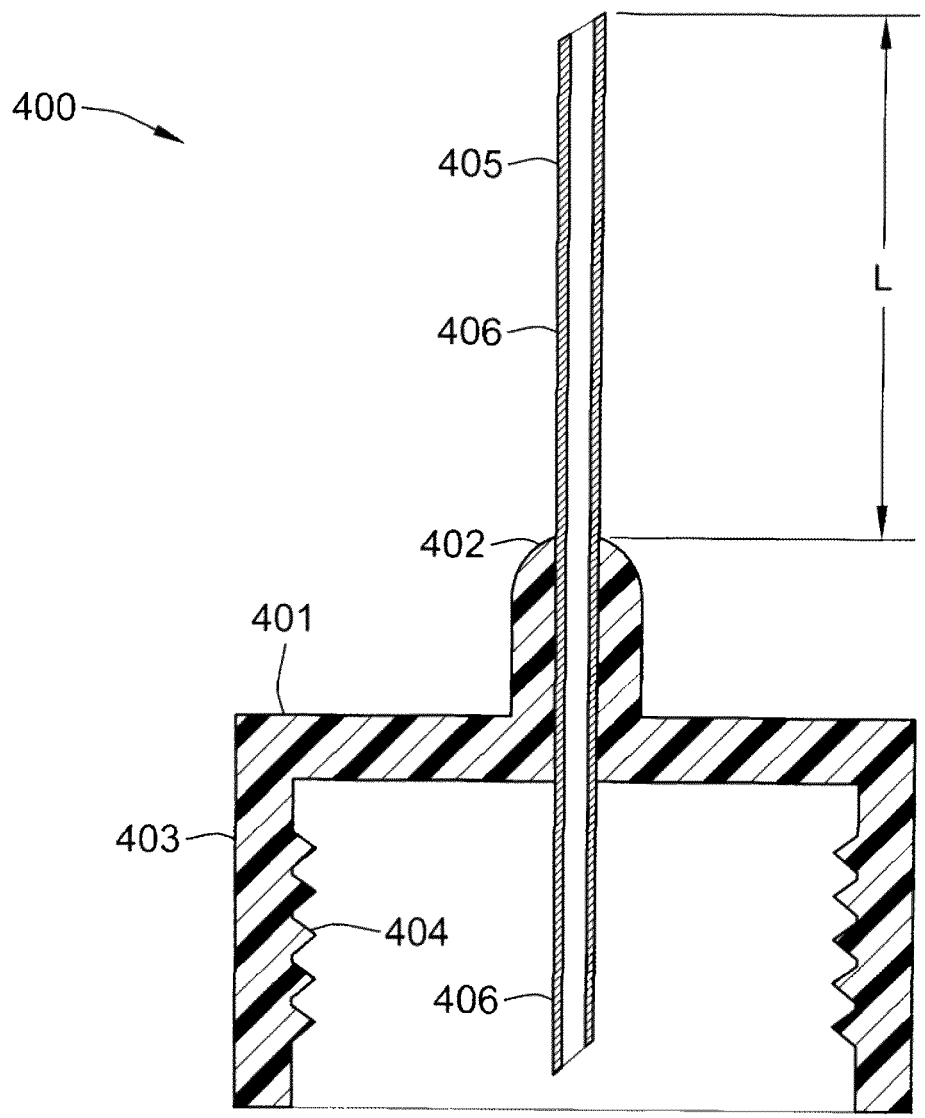
FIG. 6 illustrates one arrangement of needle assembly that may be mounted on a distal end of the delivery device.
Figure 7:
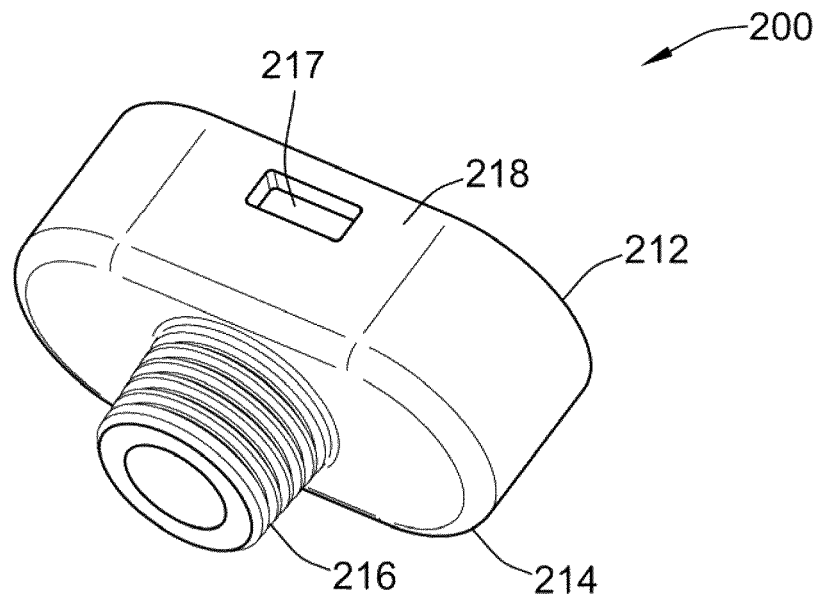
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
  a. a main outer body 210,
  b. an first inner body 220,
  c. a second inner body 230,
  d. a first piercing needle 240,
  e. a second piercing needle 250,
  f. a valve seal 260, and
  g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
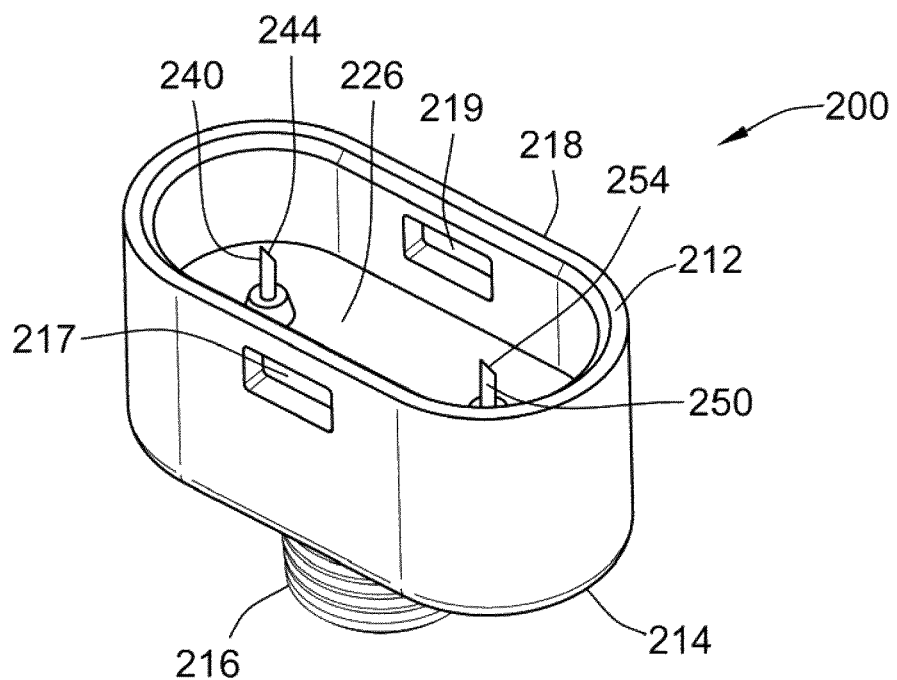
FIG. 8 illustrates another perspective view of the dispense interface illustrated in FIG. 4.
Figure 9:
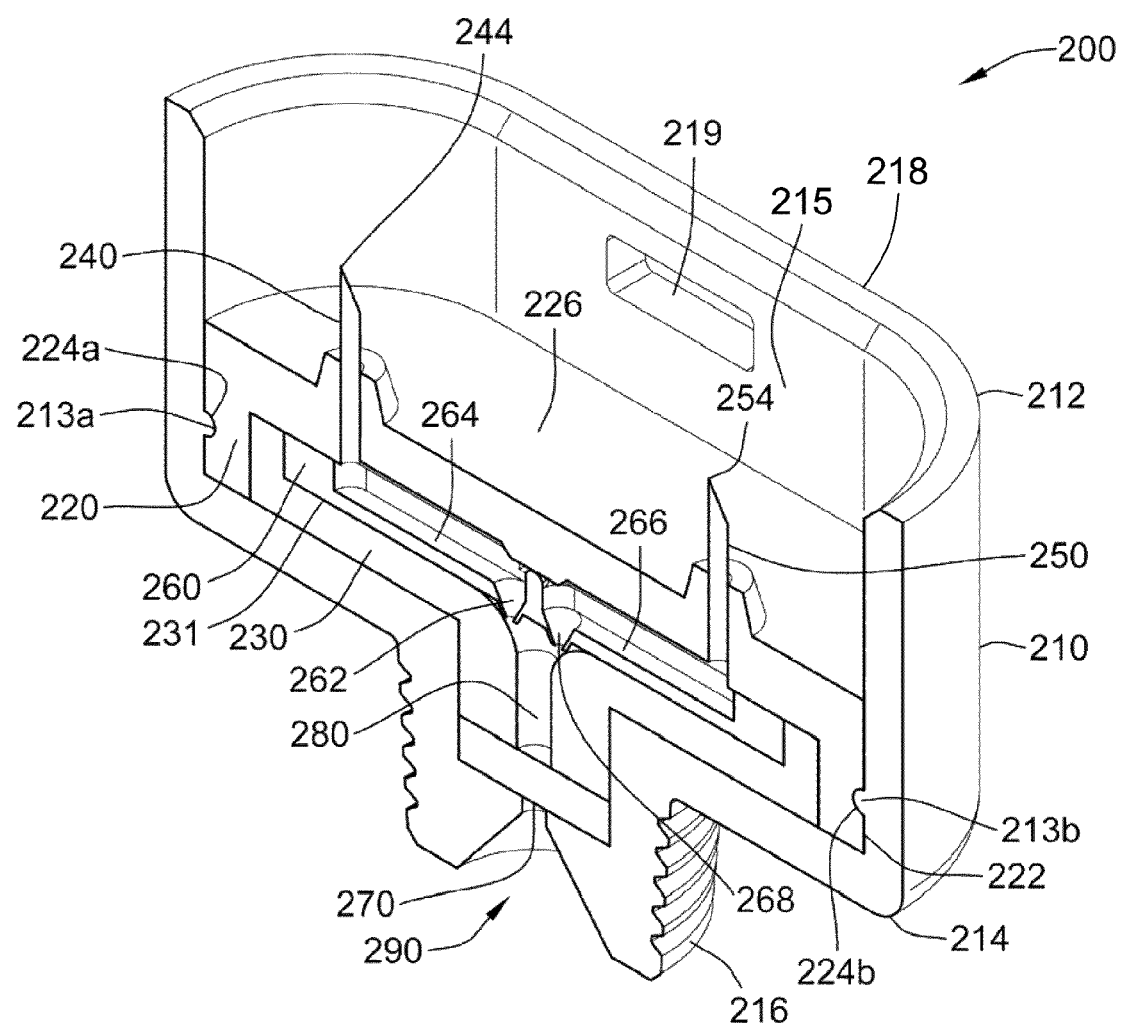
FIG. 9 illustrates a cross-sectional view of the dispense interface illustrated in FIG. 4.
Figure 10:
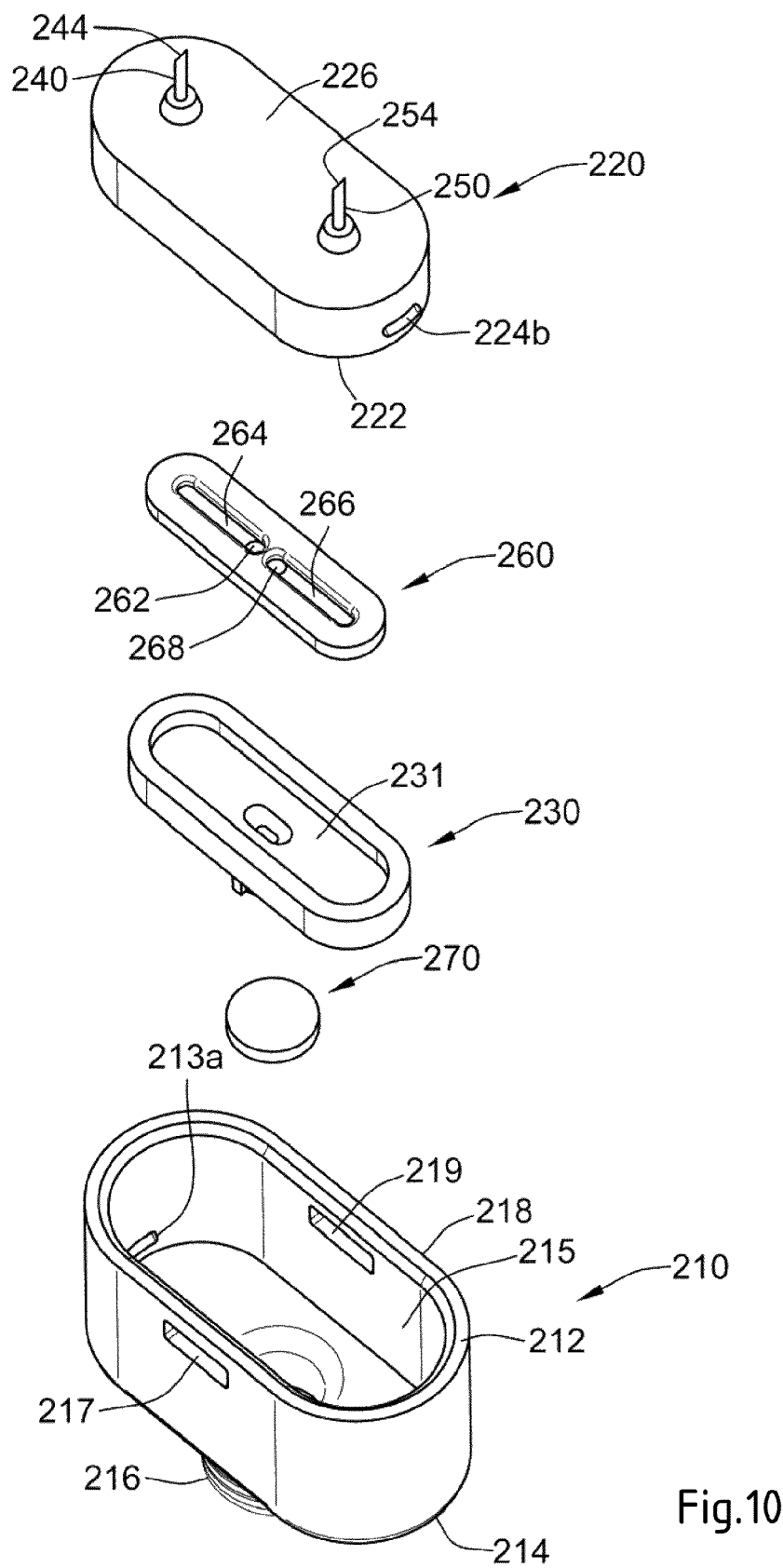
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
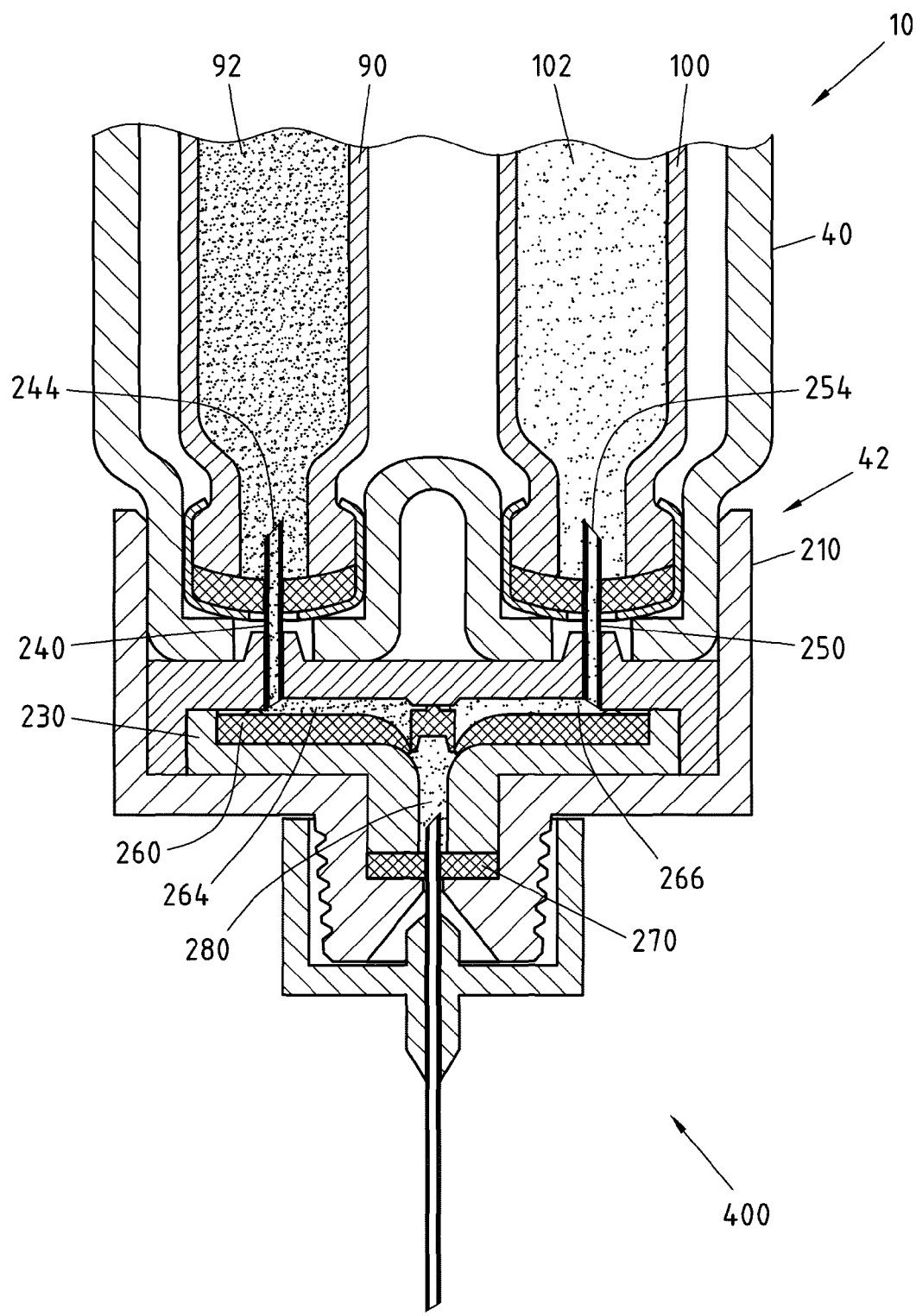
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

In the following, embodiments of the present invention will be described in detail with reference to FIGS. 12 to 23.

Figure 12:
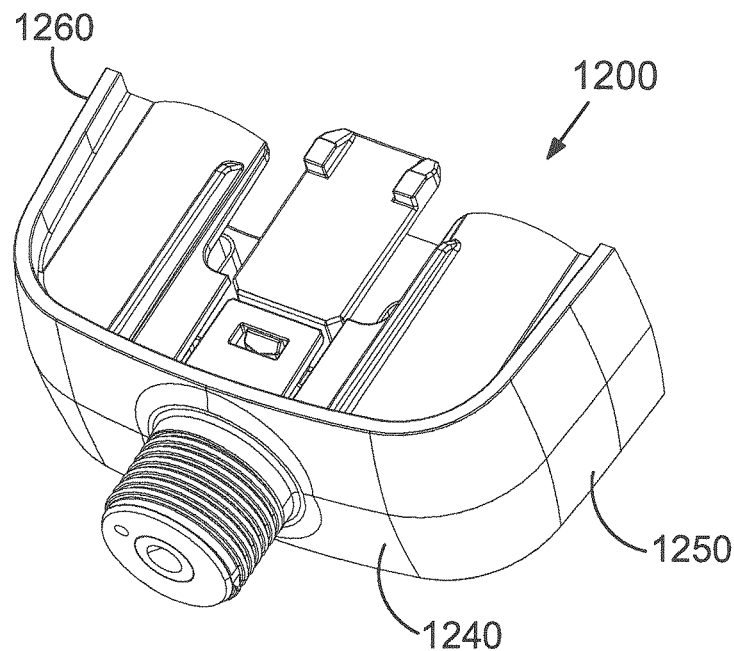
FIG. 12 illustrates a perspective view of an alternative dispense interface.
Figure 13:
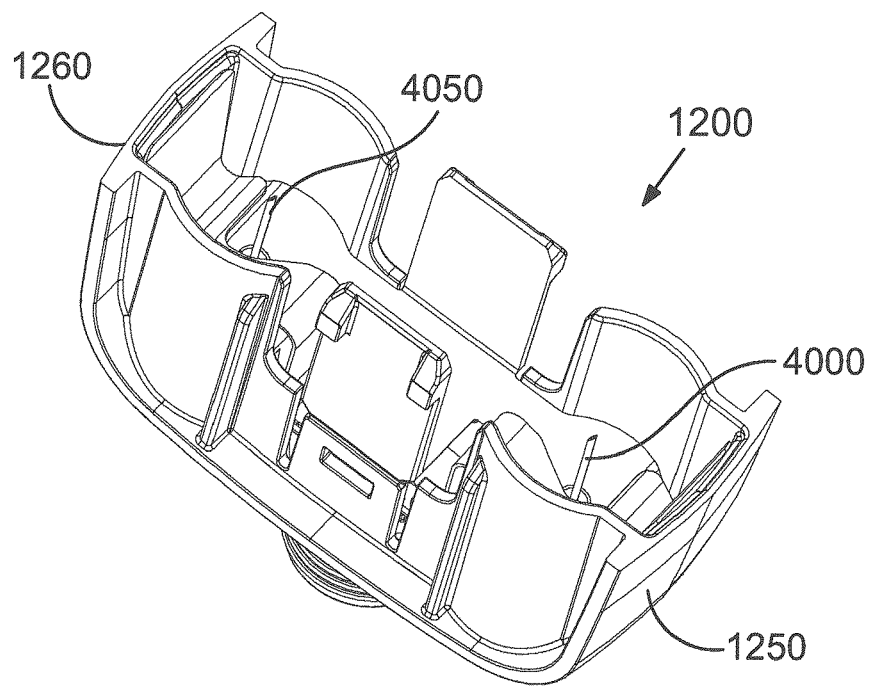
FIG. 13 illustrates another perspective view of the dispense interface illustrated in FIG. 12.
Figure 14:
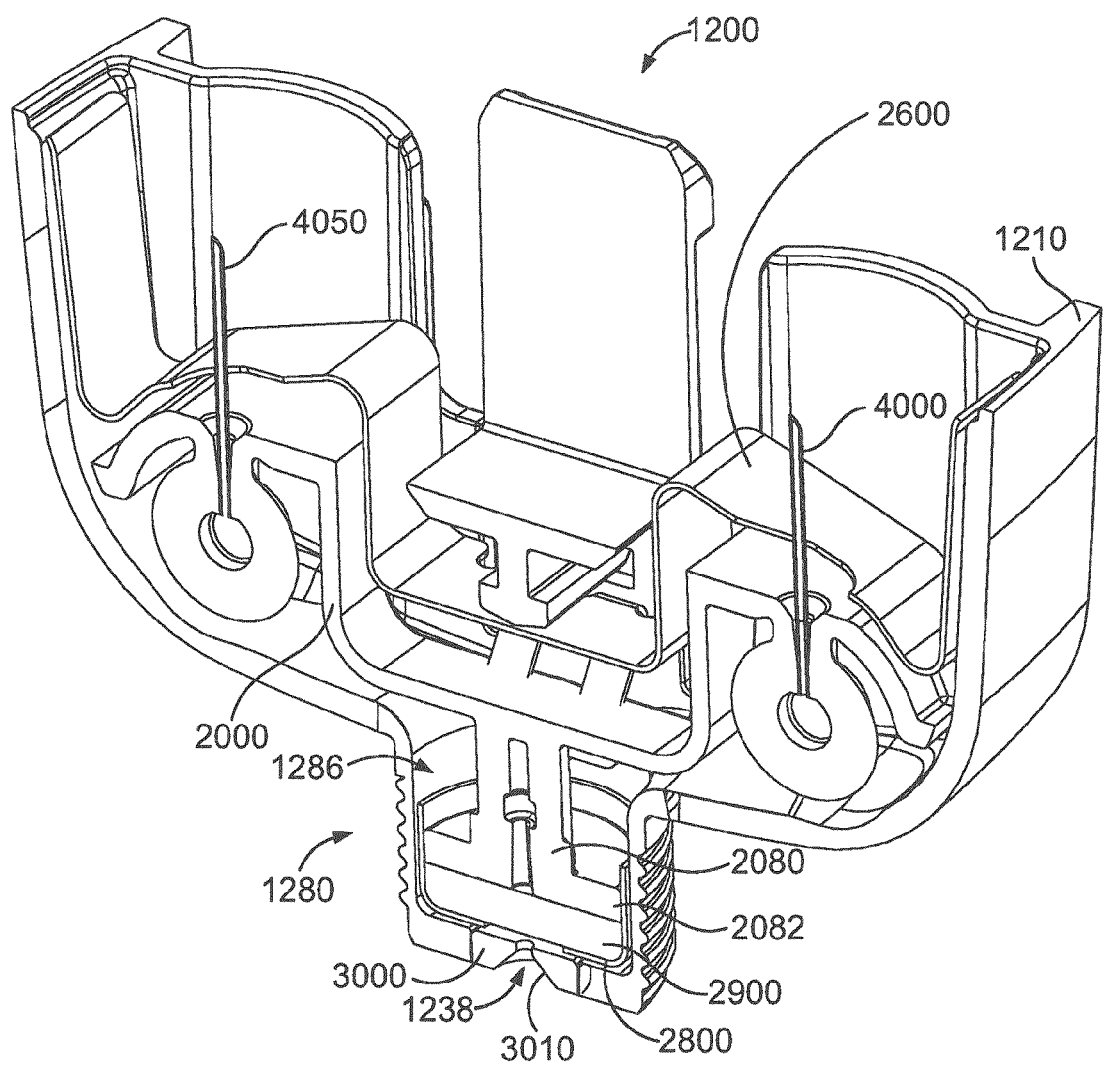
FIG. 14 illustrates a cross-sectional view of the dispense interface illustrated in FIG. 12-13.

FIG. 12 illustrates a perspective view on the distal end of one example embodiment of a dispense interface 1200. FIG. 13 illustrates a perspective view on the proximal end of the example embodiment of the dispense interface 1200 illustrated in FIG. 12, and FIG. 14 illustrates a cross-sectional view of the dispense interface 1200 illustrated in FIGS. 12 and 13. As will now be discussed in greater detail, in one preferred arrangement, the dispense interface 1200 illustrated in FIGS. 12-14 comprises:

a. a main outer body 1210;
b. an inner body 2000;
c. a manifold 2300;
d. a first piercing needle 4000;
e. a second piercing needle 4050;
f. a lock-out spring 2600;
g. a first diaphragm valve 2700;
h. a second diaphragm valve 2750;
i. a ferrule 2800;
j. an outer septum 2900; and
k. a needle guide 3000.

Figure 15:
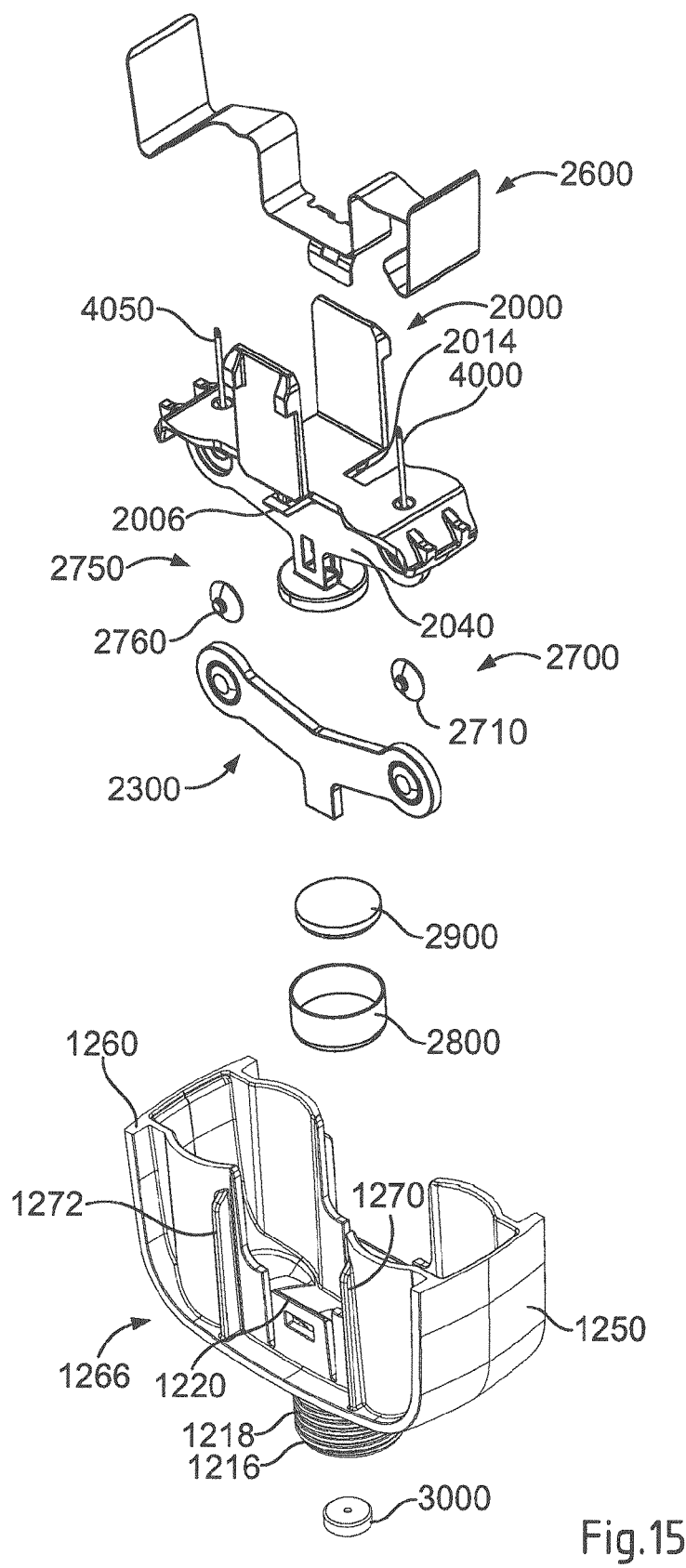
FIG. 15 illustrates an exploded view of the dispense interface illustrated in FIG. 12-13.
Figure 16:
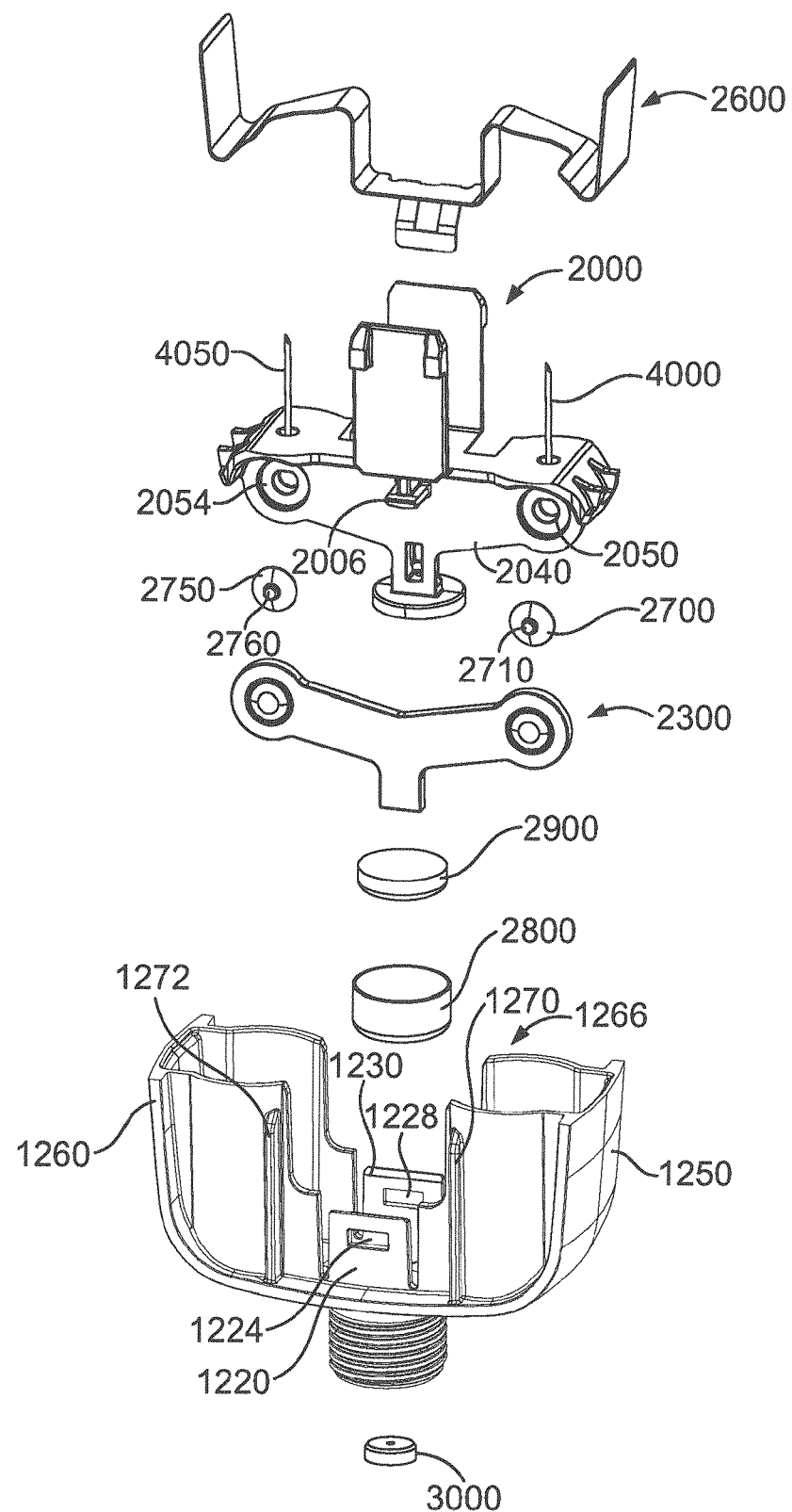
FIG. 16 illustrates an alternative exploded view of the dispense interface illustrated in FIG. 12-13.

A general interrelationship between these various component parts may be seen from FIG. 15 which illustrates one exploded perspective view of the dispense interface 1200. Similarly, FIG. 16 illustrates an alternative exploded perspective view of the dispense interface 1200.

Figure 17:
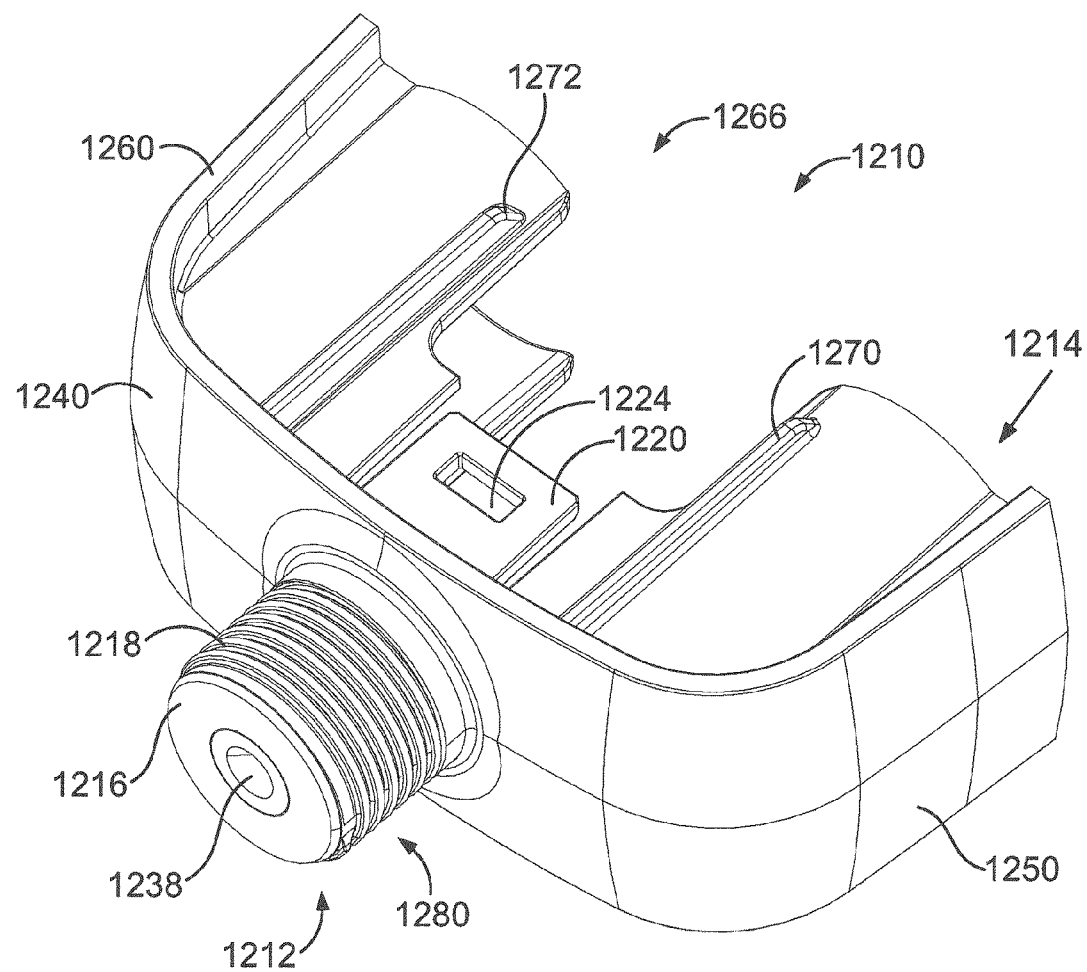
FIG. 17 illustrates a perspective view of a main outer body of the dispense interface illustrated in FIG. 15-16.

FIG. 17 illustrates a perspective view of the main outer body 1210 of the dispense interface 1200. Referring now to FIGS. 12-17, as illustrated, this body 1210 comprises a main body distal end 1212 and a main body proximal end 1214. The main body proximal end 1214 is configured to be seated along the distal end of the drug delivery device near the distal end of the cartridge holder. Preferably, the main outer body 1210 comprises an injection molded polypropylene (PP) component.

Furthermore, the main body 1210 comprises a first and a second shroud 1250, 1260 extending from the distal end to the proximal end of the main body 1210. Preferably, when the main body is assembled together with the other components of the dispense interface 1200 and the interface is attached to the drug delivery device, shrouds 1250, 1260 obscure the exposed first and second piercing needles or cannulas 4000, 4050 (see, also, e.g., FIG. 13). As such, shrouds 1250, 1260 help to prevent needle stick injuries as a user attaches the dispense interface 1200 to the drug delivery device.

As may be seen from FIGS. 12-17, a top surface 1240 of the outer body 1210 may comprise a smooth, rounded outer surface. In this illustrated outer body arrangement, the distal end of the main body of the drug delivery device comprises two flat portions that, when the dispense interface 1200 is properly connected to the drug delivery device, cover the front and back areas of the main body 1210 of the dispense interface so that an overall smooth surface is provided.

In addition and now referring to FIGS. 15-17, the main outer body 1210 further comprises two flexible connecting members 1220, 1230, one on each side of the outer body 1210. For example, the first connecting member 1220 may be seen in FIGS. 15 to 17 and the second connecting member 1230 may be seen in FIG. 16. These connecting members are positioned between the first and second shrouds 1250, 1260. Preferably, these connecting members 1220, 1230 are configured as flat tabs and constructed so as to flex outwardly (i.e., away from one another) so as allow the main outer body 1210 to be attached to and disconnected from an inner body 2000 (see, e.g., FIG. 14) of the dispense interface 1200. In one example embodiment, the two connecting members 1220, 1230 extend in a proximal direction with each flat portion comprising at least one recess. For example, as may be seen from FIG. 17, the first extending flat portion 1220 comprises at least a first recess 1224. Similarly, as may be seen from FIG. 16, the second extending flat portion 1230 comprises a second recess 1228.

Preferably, the two recesses 1224, 1228 are positioned within this main outer body 1210 so as to cooperate with a first and a second outwardly protruding members 2006, 2014 respectively, located near a middle portion of the inner body 2000. The inner body 2000 comprises a first outwardly protruding member 2006. A second similar outwardly protruding member 2014 is provided on the opposite side of the inner body portion. These outwardly protruding members 2006, 2014 of the inner body may be seen in FIG. 15.

As such, when the main body 1210 is axially positioned over the distal end of the inner body 2000 during an assembly step, the outwardly protruding members 2006, 2014 cooperate with the first and the second recess 1224, 1228 of the main outer body so as to form an interference fit, form fit, or snap lock between the two components. Preferably, such an interference fit comprises a permanent interference fit. Alternatively, and as those of skill in the art will recognize, other similar connection mechanisms that allow for the main outer body 1210 and the inner body 2000 to be axially coupled could be used as well. However, in one preferred arrangement, this connection comprises a permanent interference fit so as to prevent user manipulation of the interface in an attempt to reuse the dispense interface.

The inner body 2000 and the release button provided at the distal end of the cartridge holder of the device act to form an axially engaging snap lock or snap fit arrangement that could be axially slid onto the distal end of the cartridge housing. In an example embodiment, the dispense interface 1200 may be provided with a coding feature so as to prevent inadvertent dispense interface cross use. That is, the inner body of the hub could be geometrically configured so as to prevent an inadvertent cross use of one or more dispense interfaces.

The outer main body 1210 further comprises a guide arrangement 1266 preferably in the form of a plurality of guide ribs. The guide arrangement improves ease of fitment of the dispense interface 1200 onto the drug delivery device by properly orientating the interface 1200 during attachment. For example, as illustrated in FIGS. 15-17, two guide ribs 1270, 1272 are shown and they are provided along one side of the main body. The first guide rib 1270 is positioned between the first flat tab 1220 and the first shroud 1250. Similarly, the second guide rib 1272 is also positioned on the same side of the main body as the first rib 1270 and positioned between the first flat tab 1220 and the second shroud 1260. A similar dual guide rib arrangement is provided on the other side of the main body 1210, as shown in FIG. 15.

In this configuration, the guide rib arrangement improves ease of fitment. In one preferred arrangement, the guide rib arrangement 1266 may comprise a symmetric guide rib arrangement, so that the dispense interface may be fitted onto the distal end of the device in either orientation. In an alternative guide rib arrangement 1266, the arrangement comprises a non-symmetric arrangement where the dispense interface would not fit in either orientation to the drug delivery device.

Referring back to the main outer body 1200 illustrated in FIG. 17, a mounting hub 1216 is provided at the distal end 1212 of the main outer body 1210. Such a mounting hub 1216 may comprise a connecting mechanism 1218. Preferably, this connecting mechanism 1218 allows a needle assembly (such as the double ended needle assembly 400 illustrated in FIG. 6) to be releasably connected to the hub 1216. As just one example, this connecting mechanism 1218 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The main body mounting hub 1216 extends distally away from the outer surface 1240 of the outer body and may be generally shaped as a cylindrical extension 1280. This cylindrical extension 1280 defines an interior space 1286. This interior space 1286 may be seen from FIG. 14 which provides a cross sectional view of an assembled dispense interface 1200. At its most distal end, the connecting hub defines an aperture 1238. In an example embodiment, this aperture 1238 is appropriately sized for receiving a needle guide 3000. Preferably, the needle guide 3000 comprises a generally circular outer shape and this generally circular outer shape defines an inner recess 3010. Preferably, this inner recess 3010 comprises a conical shaped inner recess. One advantage of providing such a conical shaped inner recess is that, when a double ended needle is attached to the mounting hub 1216, the recess will guide the proximal needle of the double ended needle by the conical shaped recess 3010 into contact with a septum provided by the dispense interface 1200. This allows the proximally directed needle of the attached needle assembly to be guided through a contact path in the distal end of the inner body and then eventually into fluid communication with a holding chamber or cavity defined by the inner body 2000. By guiding the proximally directed needle of the needle assembly into a centered position, attachment of the needle assembly can be made easier. Further, the proximally directed needle may be guided into the holding chamber or cavity of the inner body 2000 more precisely.

In addition, the interior space 1286 defined by the cylindrical extension 1280 is appropriately dimensioned so as to securely position and align a ferrule 2800 and an outlet septum 2900 that are seated on a flat distal surface 2082 of a neck portion 2080 provided near a distal end of the inner body 2000. This is illustrated in the cross sectional view of the dispense interface 1200 provided in FIG. 14.

Figure 19:
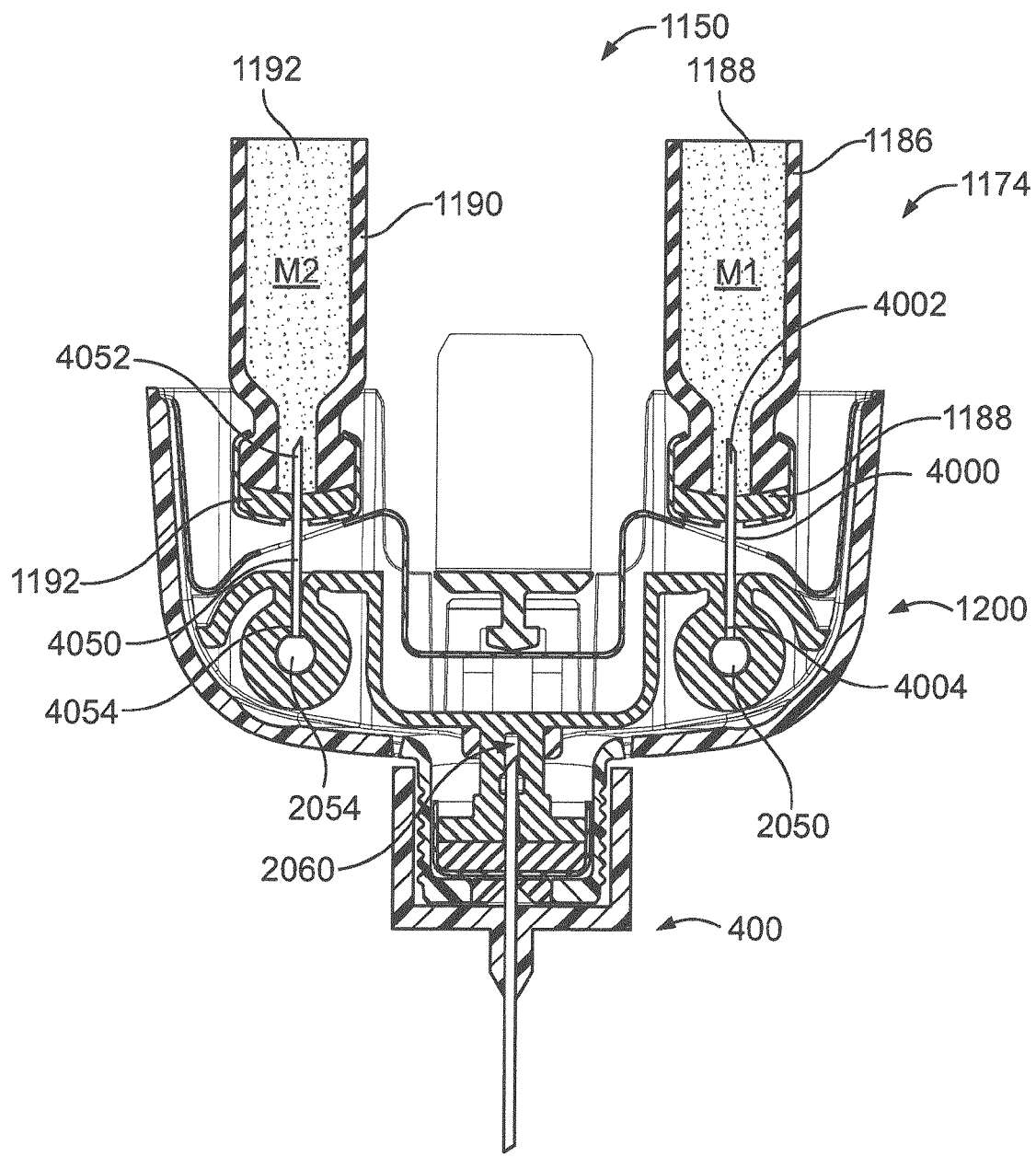
FIG. 19 illustrates a cross-sectional view of the dispense interface mounted on a drug delivery device along with a doser attached to the dispense interface.

FIG. 19 illustrates a further exemplary dispense interface 1200 after it has been mounted onto the distal end of another cartridge holder of a further drug delivery device 1150 similar to drug delivery device 10 illustrated in FIG. 1.

Figure 20:
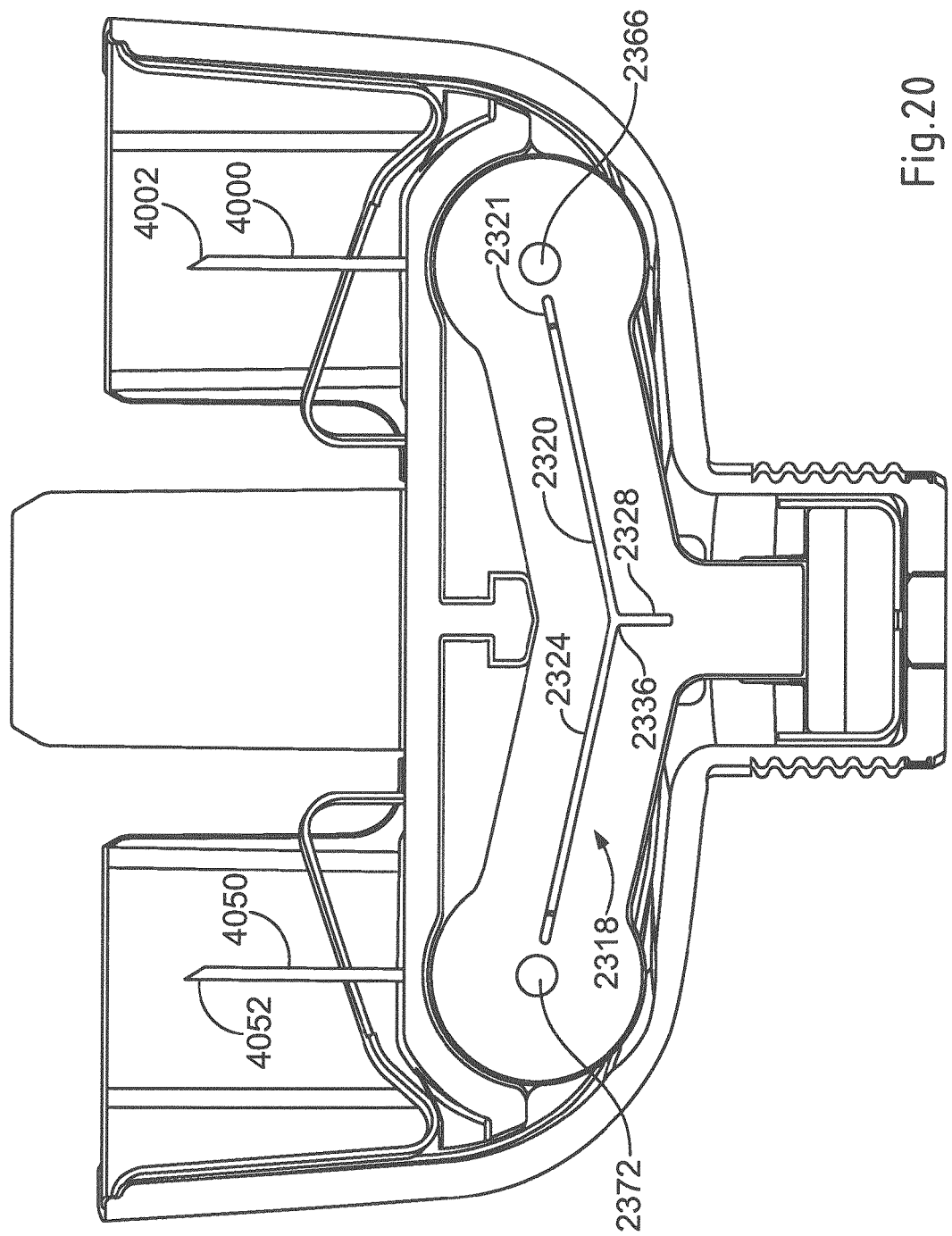
FIG. 20 illustrates a cross-sectional view of the dispense interface illustrated in FIG. 12 illustrating the fluid groove arrangement.

As illustrated, a double ended needle 400 is also mounted to the distal end of this interface. The cartridge holder 1174 is illustrated as having a first cartridge 1186 containing a first medicament 1188 and a second cartridge 1190 containing a second medicament 1192. FIG. 20 illustrates a partial cross-sectional view of the dispense interface illustrating the fluid groove arrangement 2318 of the manifold 2300. Fluid flow during a priming and dose administration step will now be explained with respect to FIGS. 19 and 20.

As illustrated in FIG. 19, the dispense interface 1200 is coupled to the distal end of a cartridge holder 1174. This cartridge holder 1174 is illustrated as containing the first cartridge 1186 containing the primary medicament 1188 and the second cartridge 1190 containing the secondary medicament 1192. Once coupled to the cartridge housing 1174, the dispense interface 1200 provides a mechanism for providing a fluid communication path from the first and second cartridges 1186, 1190 to the third cavity or the common holding chamber 2060 defined by the inner body 2000. This common holding chamber 2060 is illustrated as being in fluid communication with a doser 400. Here, as illustrated, this doser comprises the double ended needle assembly 400. As illustrated, the proximal needle of the double ended needle assembly is in fluid communication with the holding chamber 2060.

When the interface 1200 is first mounted over the distal end of the cartridge holder, the proximal piercing end 4002 of the first piercing needle 4000 pierces the septum of the first cartridge 1186 and thereby resides in fluid communication with the primary medicament 1188 of the first cartridge 1186. A distal end 4004 of the first piercing needle 4000 will also be in fluid communication with the first reservoir 2050 defined by the inner body 2000. The first diaphragm valve in the convex or unstrained state, positioned within the first valve cavity 2366 prevents the first medicament from flowing past the first reservoir and into the fluid groove arrangement 2318 defined in part by the manifold 2300.

Similarly, the proximal piercing end 4052 of the second piercing needle 4050 pierces the septum 1192 of the second cartridge 1190 and thereby resides in fluid communication with the secondary medicament 1192 of the second cartridge 1190. A distal end 4054 of this second piercing needle 4050 will also be in fluid communication with a second reservoir 2054 defined by the inner body 2000. The second diaphragm valve in the convex or unstrained state, positioned within the second valve cavity 2372 prevents the second medicament from flowing past the second reservoir and into the fluid groove arrangement 2318 defined by the manifold 2300.

To prime a dose of a medicament contained within the drug delivery device 1150, the user activates the user interface on the main body of the device as previously described herein.

In one arrangement, either the first medicament 1188 or the second medicament 1192 can be used for priming the drug delivery device system. In an alternative arrangement, both the first and the second medicaments can be used for a priming step. As just one example, if the first medicament 1188 contained within the first cartridge 1186 is used for priming, the device will activate the dosing mechanism of the drug delivery device 1150. As previously detailed herein, activating the dosing mechanism will activate a piston rod to exert pressure on a piston or stopper provided within the first cartridge 1186. As pressure builds up in the first cartridge 1186, fluidic pressure will build up in the first piercing needle 4000 and hence the first reservoir. As such, this fluidic pressure will invert the first diaphragm valve 2700. This inversion will allow the first medicament 1188 to flow out of the first reservoir 2050 of the inner body 2000, around the now inverted first diaphragm valve 2700 and then into the start point 2321 of the first fluid groove 2320 (see FIGS. 18 and 19). Under this continued pressure, the fluid will then flow into the third fluid groove 2328 and then into the holding chamber 2060 of the inner body 2000. Once in the holding chamber 2060, the fluid or medicament 1188 will then flow out the connected dispense interface 400. Similarly, if the second medicament 1192 from the second cartridge 1190 is used for priming, the second medicament 1192 will be caused to flow around the second diaphragm valve 2750, and through the second fluid groove 2324 of the manifold 2300 and then into the holding chamber 2060 of the inner body 2000 in a similar manner.

The dispense interface 1200 may be used to dispense a combined dose of the first and second medicaments in a similar manner as the priming step. For example, one possible delivery procedure may involve the following steps. First, attach a dispense interface 1200 to a distal end of the drug delivery device 1150. The dispense interface 1200 first and second needles 4000, 4050 pierce a first reservoir 1186 containing a primary compound and a second reservoir 1190 containing a secondary compound, respectively.

Next, attach a doser 400, such as a double-ended needle assembly, to a distal end of the dispense interface 1200. In this manner, a proximal end of the needle assembly 400 is in fluidic communication with both the primary compound and secondary compound residing in the holding chamber 2060. This is illustrated in FIG. 19.

Then, a user may dial up/set a desired dose of the primary compound 1188 from the injection device 1150, for example, via a graphical user interface (GUI) on the drug delivery device. Then, after the user sets the dose of the primary compound, the micro-processor controlled control unit determines or computes a dose of the secondary compound 1192 and preferably determines or computes this second dose based on a previously stored therapeutic dose profile. Where the drug delivery device includes a third medicament, the micro-processor controlled control unit computes a dose of the third medicament based on the same or a different therapeutic dose profile. It is this computed combination of medicaments that will then be injected by the user. The therapeutic dose profile may be user selectable.

Then, as previously detailed herein, activating the dosing mechanism will activate a piston rod to exert pressure on a piston or stopper provided within both the first cartridge 1186 and the second cartridge 1190 (i.e., where the device computes a combined dose of the first and second medicament). For example, as pressure builds up in both the first cartridge 1186 and the second cartridge 1190, fluidic pressure will build up in both the first and second piercing needles 4000, 4050. As such, the pressure will be built up in both the first and second reservoirs 2050, 2054 and this fluidic pressure will invert the first and second diaphragm valves. This inversion of the first valve will allow the first medicament 1188 to flow out of the first reservoir 2050, around the now inverted first diaphragm valve 2700 and then into the start point 2321 of the first fluid groove 2320 (see FIG. 20). Similarly, this inversion of the second valve will allow the second medicament 1192 to flow out of the second reservoir 2054, around the now inverted second diaphragm valve 2750 and then into the start point 2325 of the second fluid groove 2324 (see FIG. 20).

Under this continued pressure, the fluids will then flow into the third fluid groove 2328 and then into the holding chamber 2060 of the inner body 2000. Once in the holding chamber 2060, the combination of the first and second medicaments will then flow out the connected dispense interface 400.

The internal volume, otherwise referred to as ullage, of the dispense interface 1200 downstream of the first and second valves can contain an unknown mixture of the first or primary medicament (e.g., insulin) and the second or secondary medicament (e.g., GLP-1 and insulin). As just one example, where the first medicament comprises an insulin or insulin analog and the second medicament comprises a GLP-1 or GLP-1 analog, such an ullage situation may reduce dose accuracy of the drug delivery device. In particular, this situation may reduce the dose accuracy of the GLP-1 dispensed. The fluids or medicaments from the two cartridges have to pass through the downstream volume of the dispense interface prior to reaching the outlet needle. As both the first and second medicaments are present in the downstream volume, there is a potential risk that they will mix in an uncontrollable and unpredictable manner. This can cause uncertainty as to the constitution of the medicament or combined medicament that is dispensed from the outlet needle. As both medicaments contain insulin to the same concentration this uncontrollable mixing does not affect the dose accuracy of insulin as any volume of medicament leaving the outlet needle, irrespective of it's cartridge of origin, will contain the same mass of insulin. The GLP-1 is only present in one of the cartridges however and therefore dose accuracy of the GLP1 may be affected by the uncontrollable mixing that will occur in the post valve ullage.

Figure 18:
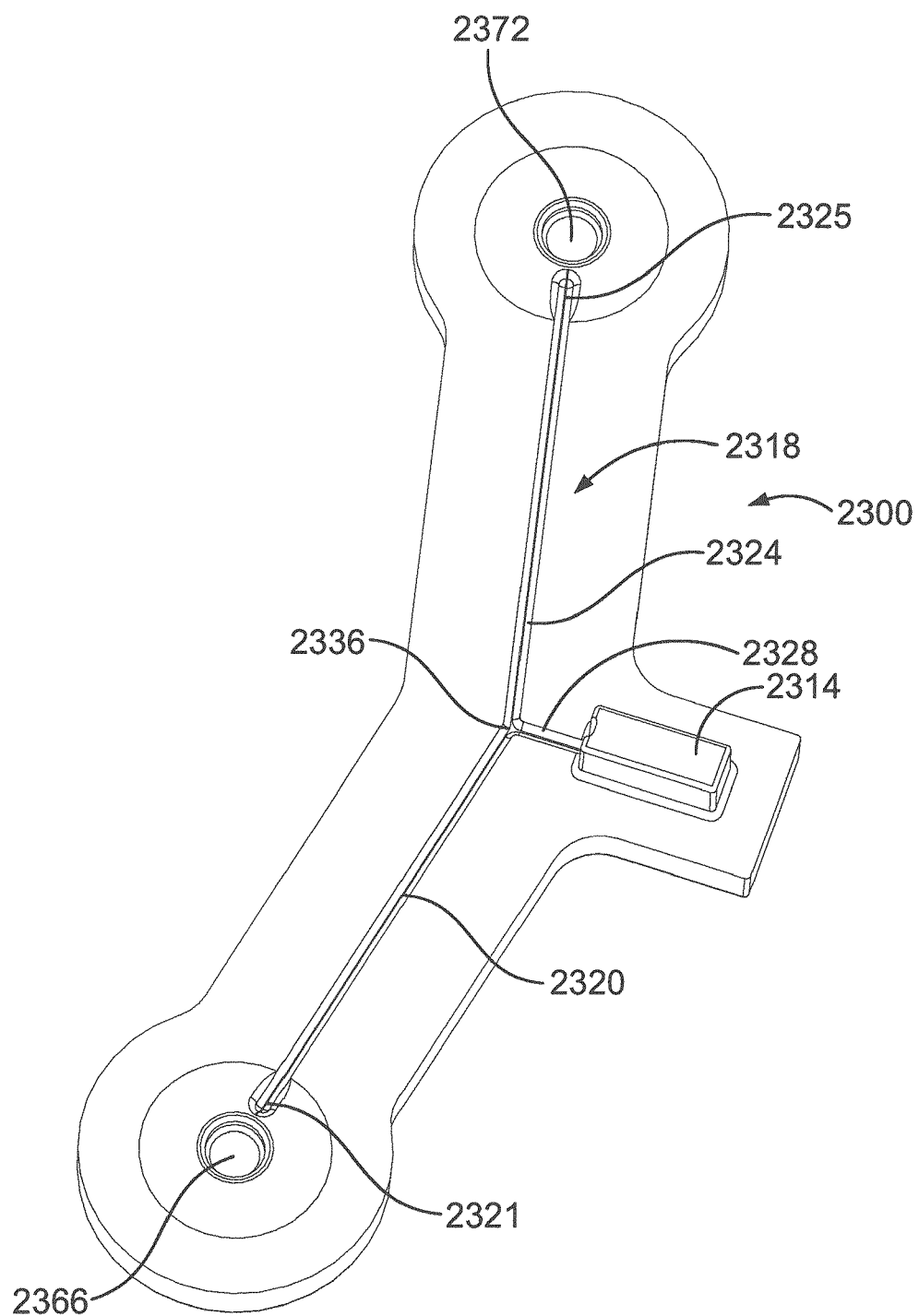
FIG. 18 illustrates a perspective view of a manifold of the dispense interface illustrated in FIG. 15-16.

In the manifold embodiment 2300 illustrated in FIG. 18 of the dispense interface 1200 previously described, this potential undesirable ullage effect may be present and may be mitigated by minimizing the post valve ullage as much as is practically feasible using existing manufacturing technology. This minimizes the problem caused by the situation of having a fluid ullage post valve shared by both medicaments, but it does not eliminate it.

Figure 21:
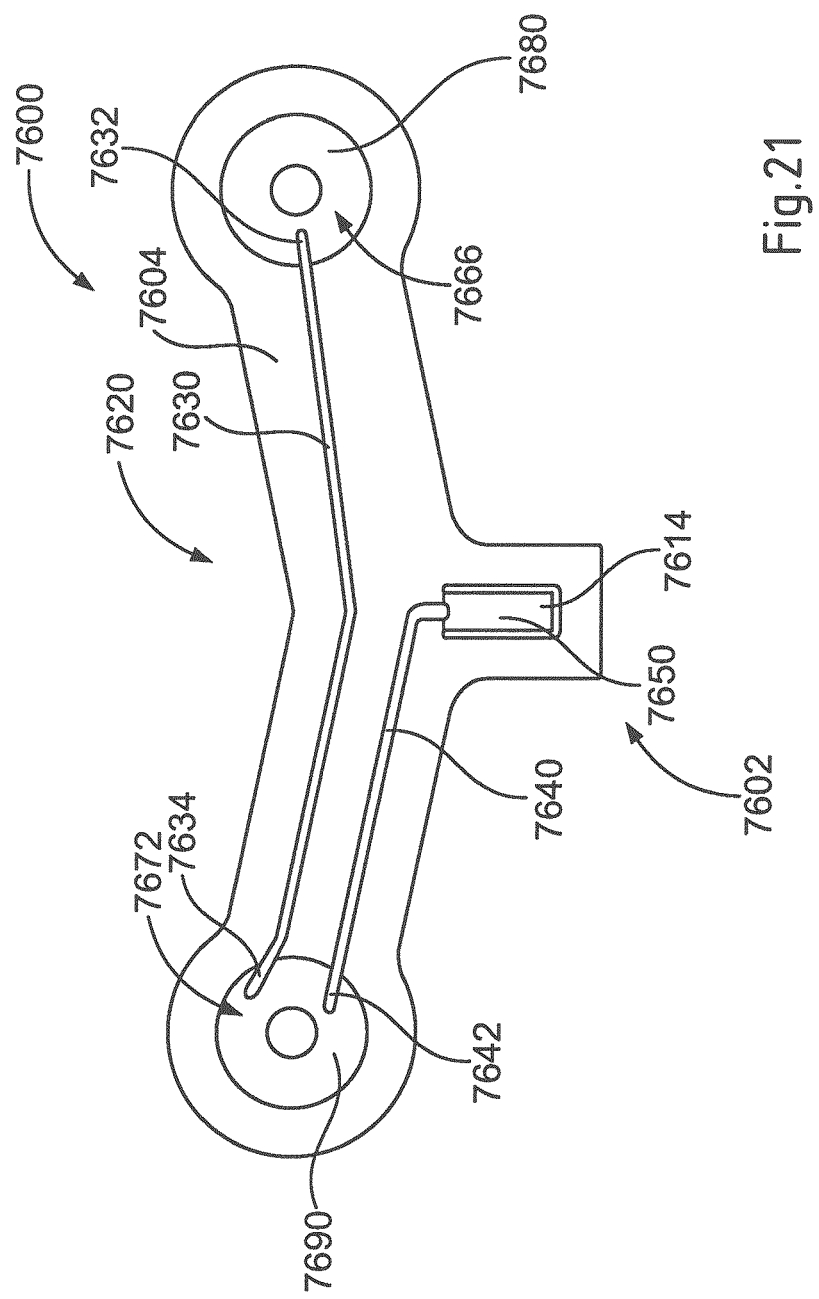
FIG. 21 illustrates a perspective view of a manifold comprising a fluid groove arrangement according to the invention.
Figure 22:
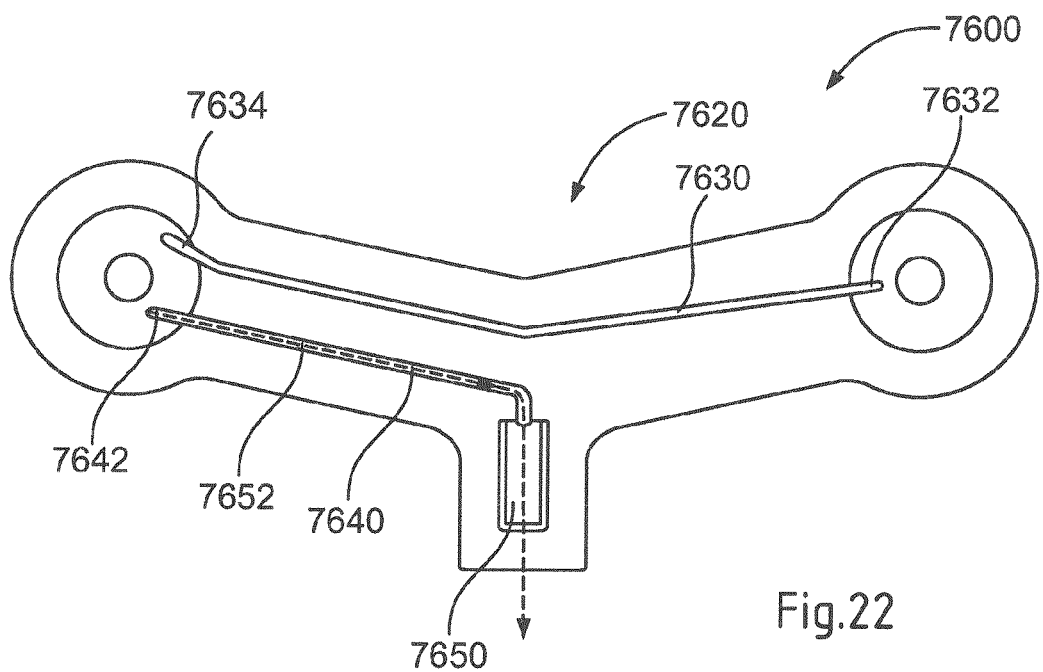
FIG. 22 illustrates a perspective view of the manifold illustrates in FIG. 21 where a first dispense of a first medicament is shown to flow by way of the fluid groove arrangement according to the invention.
Figure 23:
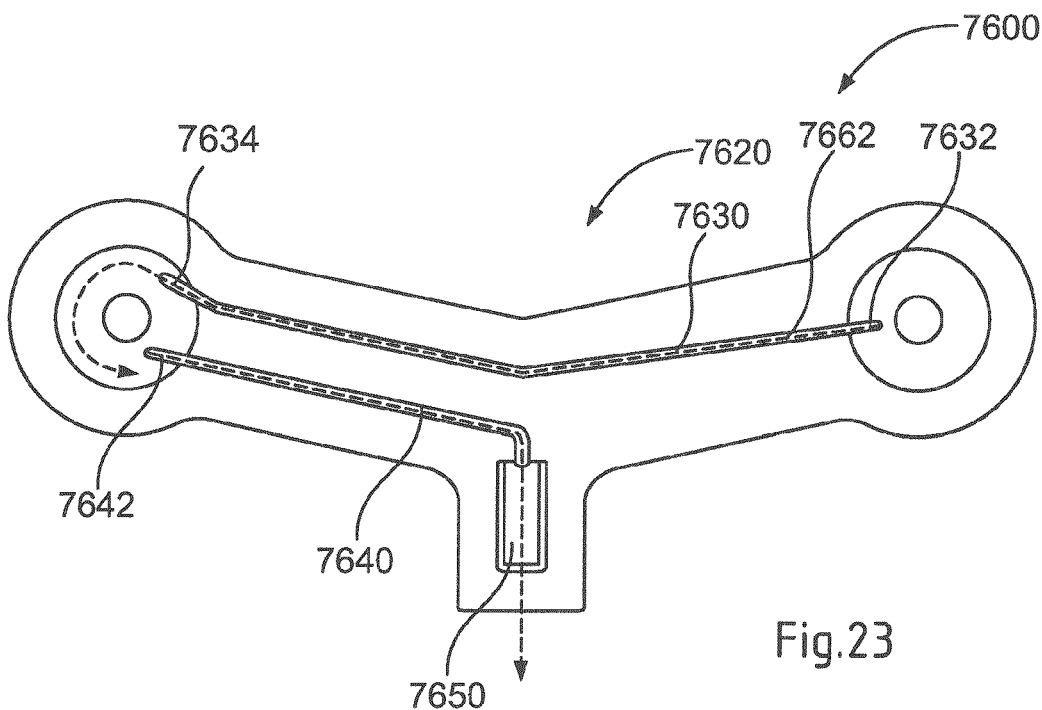
FIG. 23 illustrates a perspective view of the manifold illustrated in FIG. 21 where a second dispense of a second medicament is shown to flow by way of the fluid groove arrangement according to the invention.

FIGS. 21-23 illustrate a manifold 7600 comprising an alternative fluid groove arrangement 7620 for use with a dispense interface, such as dispense interface 1200. This alternative fluid groove arrangement offers one potential solution to the potential ullage issue described above and potentially improves the dose accuracy of the drug delivery device with respect to the first medicament delivered.

As described in greater detail below, one key feature in the alternative fluid groove arrangement 7620 is to change the fluid groove arrangement of the fluid channels between the two valves for each medicament. For example, in the embodiment illustrated in FIG. 18, the fluid grooves or channels 2320, 2324 from each valve connect to each other at a junction 2336 positioned midway between the valves. Schematically this embodiment can be represented by a 'Y'. A certain level mixing of the first and second medicaments may occur in the post valve ullage with this "Y" configuration. During a subsequent priming step, air may be pressed into the "not-primed" or "un-primed" branch of the 'Y' configuration and vice-versa when the device is switched to prime the other branch of the 'Y' configuration. During a subsequent injection step, the system may toggle air around in the branches, and the air may remain in the system. This is a potential cause for dose inaccuracy. In addition, if the entrapped air will be injected rather than medicament, that amount of drug may be missing in the dose administration and therefore may result in an underdose.

By arranging the valves sequentially, for example in a "Z" configuration instead of in a 'Y' configuration, it is possible for the secondary valve to be placed downstream of the valve for the cartridge containing the primary medicament (e.g., insulin).

By arranging the first and second valves sequentially, the flow of medicament from the primary medicament (such as insulin) valve can be used to flush or rinse any of the second medicament (the GLP-1) that may be present in the post valve ullage. To achieve this, the secondary valve must be positioned downstream of the primary valve, and the secondary medicament must be dispensed first followed by the primary medicament.

FIGS. 21-23 illustrate a manifold 7600 comprising an alternative groove arrangement 7620 for achieving sequential flow of the secondary and then the primary medicament. For example, FIG. 21 illustrates one arrangement of a manifold 7600 having an alternative fluid groove arrangement 7620 in the general shape of a "Z."

As illustrated, the manifold 7600 comprises a fluid groove arrangement 7620 and a rectangular protrusion or filling block 7614. Both the groove arrangement 7620 and the protrusion or filling block 7614 may be provided along a manifold top surface 7604. The protrusion 7614 may be provided near a distal end 7602 of the manifold 7600. In one preferred arrangement, this protrusion comprises a rectangular protrusion similar in configuration and operation as the rectangular protrusion 2314 illustrated in FIG. 18. With such a rectangular configuration, once the manifold 7600 is assembled (for example laser welded) along a flat surface of an inner body, the protrusion 7614 will reside within the third cavity or holding chamber 2060 of the inner body 2000.

As illustrated in FIG. 21, the manifold further comprises a first valve cavity 7666 and a second valve cavity 7672 provided along its top surface 7604. These cavities 7666, 7672 operate in a similar manner as the cavities illustrated in FIG. 18 and discussed herein. As such, the first valve cavity 7666 is positioned in the center of a first convex protrusion 7680 situated along the top surface 7604 of the manifold 7600. In such an arrangement, when the circular protrusion 2710 of the first diaphragm valve 2700 (FIGS. 15 and 16) is seated within the first valve cavity 7666, the diaphragm valve 2700 provides a fluid seal between the first circular recess or reservoir 2050 defined by the inner body 2000 and the fluid groove arrangement 7620 provided along the top surface of the manifold 7600. However, if fluidic pressure is applied upon the first diaphragm valve 2700 (e.g., during a dose priming or a dose injecting step), the first valve 2700 will change from a sealed state to an open state. In the open state, fluidic pressure inverts the naturally convex shape of the first valve 2700 so that the convex nature of the first valve inverts and thereby will reside along a top surface of the first convex protrusion 7680. In this open condition, the first diaphragm valve 2700 will allow fluid to flow from the first reservoir of the inner body 2000 and the fluid groove arrangement 7620 of the manifold 2300.

Similarly, the second valve cavity 7672 is also shaped for receiving a circular protrusion 2760 of a second circular diaphragm valve 2750 (FIGS. 15 and 16). Moreover, this second valve cavity 7672 is also positioned near an apex of a second convex protrusion 7690. The second diaphragm valve operates in a similar manner as the first diaphragm valve when fluid pressure is applied.

It is the operation of a first and second diaphragm valves 2700, 2750 along with a fluid groove arrangement 7620 that allows the first and second reservoirs 2050, 2054 of the inner body 2000 to be used for the sequential priming and dose administration of the first and/or second medicaments 1188, 1192 contained within a multiple medicament drug delivery device, such as the device illustrated in FIG. 1.

This fluid groove arrangement 7620 comprises a plurality of fluid grooves. For example, a first fluid groove 7630 is provided along the manifold top surface 7604. This first fluid groove 7630 has a first starting point 7632 near the first valve cavity 7680. In addition, the first fluid groove 7620 has an end point 7634 provided near the second valve cavity 7690 but this first fluid groove may not be in fluid communication with this second cavity.

Similarly, a second fluid groove 7640 has a starting point 7642 near the second valve cavity 7672 but is not in fluid communication with this second cavity. The second fluid groove resides in fluid communication with a fourth fluid groove 7650. In one preferred arrangement, this fourth fluid groove 7650 may be provided along an external surface of the rectangular protrusion 7614 provided along the bottom surface of the manifold 7600. As such, when the top surface of manifold 7600 is positioned along the generally flat surface 2040 of the inner body 2000 and then laser welded, the manifold 7600 and these plurality of fluid grooves allow for sequential fluid communication between the first and second reservoirs 2050, 2054 of the inner body 2000 and the holding chamber of the inner body 2000.

To begin the sequential flow of the two medicaments (e.g., either during a priming step or an injecting step), the secondary valve seated within the second valve cavity 7690 will be placed in an open or non-steady state where pressure is exerted upon the convex diaphragm valve. As this second valve will come under stress and the sealed convex nature of the diaphragm valve will be inverted, such that the valve will fold back towards the convex protrusion of the manifold. In this open position, the valve will therefore allow for fluid communication between the inner body second reservoir and the start portion of the second fluid groove 7642. This first fluid flow of the secondary medicament is illustrated in FIG. 22 where the only fluid flow is that the secondary medicament 7652 begins to flow from the start point 7642 of the second groove 7640 and then move towards the holding chamber and also the fourth groove 7650 of the manifold.

The first diaphragm valve operates in a similar manner to allow fluid to flow from the primary reservoir along the first section of the groove towards the end point. For example, once the secondary valve is inverted, the primary medicament 7662 will then begin to flow from the start point 7632 of the first groove 7630 and then towards the end point of the first groove. The primary medicament 7662 flows from the end point of the first groove to the start point of the second groove, passing by the second valve. The secondary medicament then flows towards the holding chamber and the fourth groove 7650 of the manifold 7600. As such, any residual of the secondary medicament 7652 present downstream of the first or primary valve is dispensed from the dispense interface 1200 during the subsequent dispense of the primary medicament.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:
1. A manifold comprising:
a first valve receptacle;
a second valve receptacle;
a first fluid groove having a starting point near or at the first valve receptacle and an end point near or at the second valve receptacle;
a second fluid groove having a starting point near or at the second valve receptacle,
a filling block, wherein the filling block is a rectangular protrusion; and a fluid connection between the second fluid groove and the filling block wherein the second valve receptacle provides fluid communication between the first fluid groove and the second fluid groove; and wherein the filling block, the first fluid groove, and the second fluid groove are arranged on a surface of the manifold.

2. The manifold according to claim 1, wherein the first valve receptacle is a first valve cavity and the second valve receptacle is a second valve cavity.

3. The manifold according to claim 1, wherein each of the first valve receptacle and the second valve receptacle is positioned in a respective convex protrusion on a surface of the manifold.

4. The manifold according to claim 3, wherein each of the first valve receptacle and the second valve receptacle is positioned in the center of the respective convex protrusion.

5. The manifold according to claim 1, wherein the outward appearance of the manifold is Y-shaped.

6. An apparatus comprising:
a manifold comprising:
a first valve receptacle;
a second valve receptacle; and
a fluid groove arrangement comprising a first fluid groove and a second fluid groove;
wherein the first fluid groove has a starting point near or at the first valve receptacle and an end point near or at the second valve receptacle,
wherein the second fluid groove has a starting point near or at the second valve receptacle, and
wherein the second valve receptacle provides fluid communication between the first fluid groove and the second fluid groove;
an inner body of a dispense interface, wherein the inner body comprises a holding chamber configured for housing a filling block and further configured for fluid outflow from the inner body;
a first valve structure at least partially received by the first valve receptacle;
a second valve structure at least partially received by the second valve receptacle;
a first reservoir defined by the inner body;
a second reservoir defined by the inner body;
wherein the first valve structure is configured, in a first state, to provide a fluid seal between the first reservoir and the fluid groove arrangement and configured, in a second state, to enable fluid flow from the first reservoir to the fluid groove arrangement,
wherein the second valve structure is configured, in a first state, to provide a fluid seal between the second reservoir and the fluid groove arrangement and configured, in a second state, to enable fluid flow from the second reservoir to the fluid groove arrangement, and
wherein the inner body is arranged with the manifold such that any fluid flowing from the first reservoir to the holding chamber via the first valve structure or any fluid flowing from the second reservoir to the holding chamber via the second valve structure flows first through the second fluid groove.

7. The apparatus according to claim 6, wherein the first valve structure is configured to block fluid flow from the first reservoir to the starting point of the first fluid groove in a first state and to enable fluid flow from the first reservoir to the starting point of the first fluid groove in a second state.

8. The apparatus according to claim 6, wherein the second valve structure is configured to block fluid flow from the second reservoir to the starting point of the second fluid groove in a first state and to enable fluid flow from the second reservoir to the starting point of the second fluid groove in a second state.

9. The apparatus according to claim 6, wherein the first valve structure comprises a diaphragm valve the diaphragm valve comprising a circular protrusion configured to be seated in the first valve receptacle, wherein the diaphragm valve is substantially cup-shaped, and wherein in a first state the diaphragm valve is facing the first valve receptacle with the diaphragm valve's convex side and is un-stressed.

10. The apparatus according to claim 9, wherein the diaphragm valve is configured to invert its cup-shape under fluidic pressure and wherein the cup-shape of the diaphragm valve is inverted in a second state.

* * * * *